(12) United States Patent
Medina et al.

(10) Patent No.: US 10,916,903 B2
(45) Date of Patent: Feb. 9, 2021

(54) SYSTEM HAVING A CABLE ASSEMBLY AND PLUG AND RECEPTACLE CONNECTORS

(71) Applicants: Creganna Unlimited Company, Galway (IE); TYCO ELECTRONICS JAPAN G.K., Kawasaki (JP)

(72) Inventors: Thomas Medina, Portland, OR (US); Yohichi Sasaki, Kawasaki (JP); Makiya Kimura, Kodaira (JP)

(73) Assignees: CREGANNA UNLIMITED COMPANY, Galway (IE); TYCO ELECTRONICS JAPAN G.K., Kawasaki (JP)

( * ) Notice: Subject to any disclaimer, the term of this patent is extended or adjusted under 35 U.S.C. 154(b) by 0 days.

(21) Appl. No.: 16/264,872

(22) Filed: Feb. 1, 2019

(65) Prior Publication Data
US 2019/0245310 A1    Aug. 8, 2019

Related U.S. Application Data

(60) Provisional application No. 62/626,150, filed on Feb. 4, 2018, provisional application No. 62/626,161, filed on Feb. 5, 2018.

(51) Int. Cl.
*H01R 27/02*    (2006.01)
*H01R 12/53*    (2011.01)
(Continued)

(52) U.S. Cl.
CPC ......... *H01R 27/02* (2013.01); *A61M 25/0097* (2013.01); *H01R 12/53* (2013.01);
(Continued)

(58) Field of Classification Search
CPC ........ H01R 24/58; H01R 24/60; H01R 27/02; H01R 13/625; H01R 12/53; H01R 12/714;
(Continued)

(56) References Cited

U.S. PATENT DOCUMENTS 6,179,824 B1 * 1/2001 Eggers ................ A61B 18/148
                                                          604/500
6,663,570 B2 * 12/2003 Mott .................... A61B 5/0215
                                                          439/909
(Continued)

FOREIGN PATENT DOCUMENTS

WO        9833428 A2    8/1998
WO     2013154684 A1   10/2013
WO     2017189092 A1   11/2017

OTHER PUBLICATIONS

"Interventional Catheters/Medical Catheter Shaft Design & Manufacturing" TE Connectivity; 2014 (4 pages).
(Continued)

*Primary Examiner* — Hien D Vu

(57) ABSTRACT

Catheter assembly includes a cable assembly. The cable assembly includes first and second cable segments that are interconnected by a plug connector and a receptacle connector. The plug connector includes an elongated plug substrate and a mating array of electrical contacts supported by the plug substrate. The receptacle connector includes a system array of electrical contacts. The receptacle housing is sized and shaped to receive the plug substrate during a mating operation.

23 Claims, 22 Drawing Sheets

(51) Int. Cl.
*H01R 12/72* (2011.01)
*A61M 25/00* (2006.01)
*H01R 12/71* (2011.01)
*A61B 5/0215* (2006.01)
*H01R 12/73* (2011.01)
*A61B 5/01* (2006.01)
*A61B 5/00* (2006.01)
*A61B 8/00* (2006.01)
*A61B 17/00* (2006.01)
*A61B 18/00* (2006.01)
*A61M 39/10* (2006.01)
*H01R 13/625* (2006.01)

(52) U.S. Cl.
CPC ......... *H01R 12/714* (2013.01); *H01R 12/721* (2013.01); *A61B 5/01* (2013.01); *A61B 5/0215* (2013.01); *A61B 5/6852* (2013.01); *A61B 8/445* (2013.01); *A61B 2017/00292* (2013.01); *A61B 2018/00577* (2013.01); *A61B 2562/227* (2013.01); *A61M 2039/1022* (2013.01); *H01R 12/73* (2013.01); *H01R 13/625* (2013.01); *H01R 2201/12* (2013.01)

(58) Field of Classification Search
CPC ....... H01R 12/721; A61B 5/01; A61B 5/6852; A63M 25/0097

USPC ....................................................... 604/500
See application file for complete search history.

(56) References Cited

U.S. PATENT DOCUMENTS

| | | | |
|---|---|---|---|
| 8,342,887 B2 * | 1/2013 | Gleason | A61B 1/00124 |
| | | | 439/668 |
| 8,430,685 B2 | 4/2013 | Brekosky et al. | |
| 9,368,885 B2 | 6/2016 | Sakamoto | |
| 9,812,801 B2 * | 11/2017 | Okura | H01B 7/08 |
| 10,264,995 B2 * | 4/2019 | Brister | A61B 5/0028 |
| 10,537,306 B2 * | 1/2020 | Schaer | A61B 8/0891 |
| 2010/0062633 A1 | 3/2010 | Puttinger et al. | |
| 2013/0144253 A1 | 6/2013 | Ryan et al. | |
| 2013/0296729 A1 | 11/2013 | Datta | |
| 2014/0127922 A1 | 5/2014 | Sasaki | |
| 2015/0162684 A1 * | 6/2015 | Amini | H01R 24/60 |
| | | | 439/660 |
| 2016/0322730 A1 | 11/2016 | Sasaki et al. | |
| 2016/0322746 A1 | 11/2016 | Sasaki et al. | |

OTHER PUBLICATIONS

International Search Report dated Apr. 15, 2019, for corresponding International Application No. PCT/US2019/016532.

* cited by examiner

SYSTEM HAVING A CABLE ASSEMBLY AND PLUG AND RECEPTACLE CONNECTORS

CROSS-REFERENCE TO RELATED APPLICATION

The present application claims the benefit of U.S. Provisional Application No. 62/626,150, filed on Feb. 4, 2018, and U.S. Provisional Application No. 62/626,161, filed on Feb. 5, 2018, each of which is incorporated herein by reference in its entirety.

BACKGROUND

Catheter assemblies are medical instruments that can be inserted into a body (human or animal) to treat disease, perform surgery, image, detect physiological information, and the like. For many applications, the catheter assembly communicates data signals from a device that generates the data signals to a control system (or control device). For example, an ultrasound probe that is inserted into the body may communicate image data through a cable to a control system, such as a desktop computer or tablet computer. Electrical power may also be supplied to the device through the cable. The cable may include a tube and other optional components, such as a shaft that is inserted into the body.

Communicating signals and supplying power through the cable of the catheter assembly while simultaneously achieving a desired flexibility or diameter can be challenging. For example, catheter assemblies having smaller diameters for inserting into a patient's body are desired but may be incapable of achieving a designated bandwidth, signal density or data throughput.

This challenge is more complex for catheter assemblies that include multiple interconnected segments. For example, two segments of a catheter assembly may be coupled through electrical connectors. An electrical connector typically includes contacts that engage respective contacts of the other electrical connector. Data signals propagating through a single channel of the catheter assembly are transmitted through the engaged contacts of the electrical connectors. As the number of channels increase, however, the number of contacts increase. Arranging the contacts of one electrical connector so that those contacts sufficiently mate with the contacts of the other electrical connector while also satisfying a designated cross-sectional size can be difficult.

BRIEF DESCRIPTION

In an embodiment, a catheter assembly is provided that includes a cable assembly. The cable assembly includes first and second cable segments that are interconnected by a plug connector and a receptacle connector. The plug connector comprising an elongated plug substrate and a mating array of electrical contacts supported by the plug substrate. The receptacle connector includes a system array of electrical contacts. The receptacle housing is sized and shaped to receive the plug substrate during a mating operation.

In an embodiment, a catheter assembly is provided that includes a cable assembly extending between proximal and distal ends and having conductive pathways extending therebetween. The distal end includes a modular device configured to be inserted into a body and configured to at least one of detect external signals or emit energy. A centerline extends through the cable assembly. The cable assembly includes first and second cable segments that are interconnected by a plug connector and a receptacle connector. The plug connector includes an elongated plug substrate and a mating array of electrical contacts supported by the plug substrate. The plug substrate projects in an axial direction along the centerline. The receptacle connector includes a receptacle housing and a system array of electrical contacts. The receptacle housing has an enclosed slot that is sized and shaped to receive the plug substrate during a mating operation in which the plug substrate is inserted into the enclosed slot in the axial direction. The system array and the mating array engage each other along a mating zone within the enclosed slot. The mating zone extends essentially parallel to the centerline.

In an embodiment, a system is provided that includes a control system and a modular device communicatively coupled through a cable assembly and a connector assembly. The modular device is configured to be inserted into a body and configured to at least one of detect external signals or emit energy. The connector assembly has a plug connector and a receptacle connector, wherein a centerline extends through the cable assembly. The plug connector includes an elongated plug substrate and a mating array of electrical contacts supported by the plug substrate. The plug substrate projects in an axial direction along the centerline. The receptacle connector includes a receptacle housing and a system array of electrical contacts. The receptacle housing has an enclosed slot that is sized and shaped to receive the plug substrate during a mating operation in which the plug substrate is inserted into the enclosed slot in the axial direction, wherein the system array and the mating array engage each other along a mating zone within the enclosed slot. The mating zone extends essentially parallel to the centerline.

In some aspects, the control system includes a panel and one of the receptacle connector or the plug connector is mounted to the panel. The other of the receptacle connector or the plug connector is coupled to a proximal end of the cable assembly.

In an embodiment, a kit is provided that includes the system described above. The cable assembly includes first and second cable segments that are interconnected by the plug connector and the receptacle connector. The first cable segment is a single-use disposable segment. The kit includes a plurality of the first cable segments that are each configured to operably engage the second cable segment.

In some aspects, the electrical contacts of at least one of the system array or the mating array includes mating segments. The mating segments are deflected along the mating zone. Optionally, the enclosed slot is defined by an interior slot surface. The mating segments include spring fingers that clear the interior slot surface and are deflected toward the interior slot surface.

In some aspects, the plug connector includes a plug housing having a mating cavity that is configured to receive the receptacle connector. The mating cavity is defined by an interior wall surface that surrounds the centerline. The plug housing and the receptacle housing are configured to pluggably engage each other such that the interior wall surface surrounds the receptacle housing.

In some aspects, the mating array includes at least 40 electrical contacts that are coplanar with respect to one another. The catheter assembly has an outer diameter at the plug connector that is at most 45 millimeters (mm).

In some aspects, the electrical contacts of the system array are movable, as a group, in a radial direction that is perpendicular to the centerline.

In some aspects, each of the plug connector and the receptacle connector includes a secondary array of electrical contacts. The secondary arrays engage each other during the mating operation, wherein the mating array and system array communicate data signals of a first type. The secondary arrays communicate at least one of electrical power or data signals of a second type.

In some aspects, the plug connector also includes electrical terminals and conductors that extend between the electrical terminals and the electrical contacts and through the plug substrate. The electrical terminals are mechanically and electrically coupled to the conductive pathways.

In some aspects, the receptacle housing has an exterior surface that defines a cross-sectional profile taken perpendicular to the centerline. The cross-sectional profile is essentially rectangular.

In an embodiment, a kit is provided that includes the catheter assembly. The first cable segment is a single-use disposable segment. The kit also includes a plurality of the first cable segments that are each configured to operably engage the second cable segment.

In an embodiment a cable segment of a catheter assembly is provided. The cable segment includes an elongated cable extending between an operating end and a mating end. The elongated cable has conductive pathways extending between the operating end and the mating end. A centerline extends through a center of the elongated cable. The cable segment also includes a plug connector coupled to the elongated cable at the mating end. The plug connector includes a plug housing having a mating cavity that is configured to receive another connector. The mating cavity is defined by an interior wall surface that surrounds the centerline. The plug connector also includes a plug substrate extending along the centerline within the mating cavity such that a connector-receiving space circumscribes the plug substrate. The plug substrate supports a two-dimensional (2D) mating array of electrical contacts that are oriented parallel to the centerline.

In some aspects, the interior wall surface defines a cross-sectional profile of the mating cavity that is taken perpendicular to the centerline. The cross-sectional profile is essentially rectangular.

In some aspects, the mating array includes at least 40 electrical contacts that are coplanar with respect to one another. The catheter assembly has an outer diameter at the plug connector that is at most 45 millimeters (mm).

In some aspects, the cable segment is a single-use disposable segment.

In some aspects, the plug connector also includes electrical terminals and conductors that extend between the electrical terminals and the electrical contacts and through the plug substrate. The electrical terminals are mechanically and electrically coupled to the conductive pathways.

In an embodiment, a cable segment of a catheter assembly is provided. The cable segment includes an elongated cable extending between an operating end and a mating end. The elongated cable has conductive pathways extending between the operating end and the mating end. A centerline extends through a center of the elongated cable. The cable segment also includes a receptacle connector having a receptacle housing and a system array of electrical contacts. The receptacle housing defines an enclosed slot that is sized and shaped to receive a plug substrate from another connector. The enclosed slot opens in an axial direction that is parallel to the centerline. The system array is configured to engage a mating array along the plug substrate within the enclosed slot.

In some aspects, the electrical contacts of the system array include mating segments. The enclosed slot is defined by an interior slot surface. The mating segments are configured to clear the interior slot surface and be deflected toward the interior slot surface.

DETAILED DESCRIPTION

Figure 1:
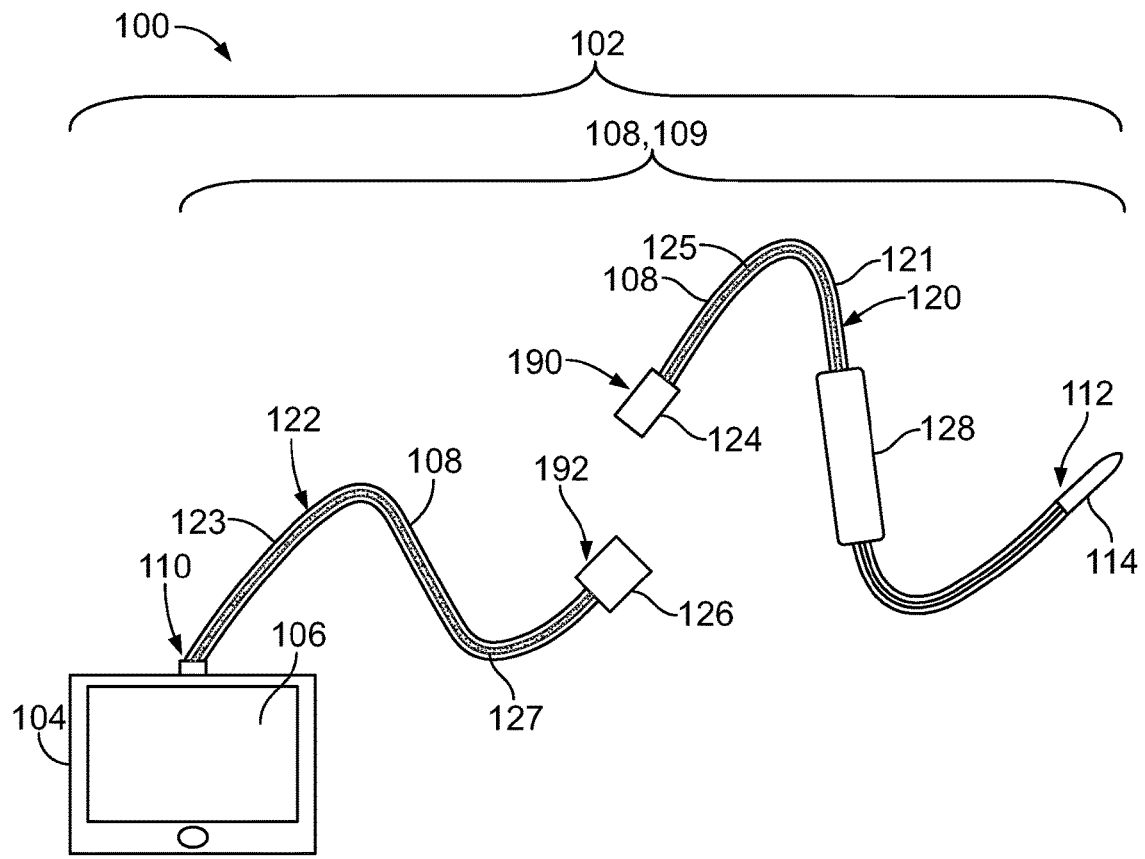
FIG. 1 is a schematic view of a system having a catheter assembly formed in accordance with an embodiment.

Embodiments set forth herein include catheter assemblies, cable assemblies, cable segments, and electrical connectors that include arrays of electrical contacts (referred to herein as "contact arrays"). Embodiments also include methods of manufacturing or assembling the same.

Catheter assemblies can be used in a variety of applications. Non-limiting examples include cardiovascular applications (e.g., percutaneous transluminal coronary angioplasty (PTCA), stent delivery, drug-elution, atherectomy delivery, thrombectomy, intravascular imaging, and vascular closure); peripheral vascular applications (e.g., percutaneous transluminal angioplasty (PTA), abdominal aortic aneurysm (AAA)/thoracic aortic aneurysm (TAA) stent graft delivery, advanced introducer systems, vascular closure, embolic protection, occlusion catheters, and specialty PTA catheters); structural heart applications (e.g., percutaneous valve delivery systems, valvuloplasty balloon dilation catheters, introducer sheaths, transeptal access, transapical access, sizing balloon catheters, occlusion catheters, patent foramen ovale (PFO) closure delivery devices, left atrial appendage (LAA) closure delivery systems, guiding sheaths, steerable sheaths, and dilation catheters), electrophysiology (e.g., EP diagnostic catheters for mapping and ablation, ablation catheter for atrial fibrillation, cryotherapy catheters, introducer sheaths, transeptal access systems, imaging catheters, lead placement and implantation devices, and dilation catheters), and neurovascular applications.

The contact arrays are configured to electrically interconnect portions of a catheter assembly. For example, a plug connector of one cable segment and a receptacle connector of another cable segment may each have a contact array. The electrical contacts of each array are electrically coupled to respective conductive pathways (e.g., conductors in insulated wires, conductive traces in flex circuits, and the like). The contact arrays are configured to engage each other when the plug and receptacle connectors are mated so that signals and/or power may be communicated through each of the cable segments.

In some embodiments, a contact array may include at least 40 electrical contacts. In certain embodiments, a contact array may include at least 60 electrical contacts or at least 80 electrical contacts. In particular embodiments, a contact array may include at least 100 electrical contacts or at least 125 electrical contacts. In more particular embodiments, a contact array may include at least 200 electrical contacts or at least 300 electrical contacts. Yet in more particular embodiments, a contact array may include at least 400 electrical contacts or at least 500 electrical contacts.

In some embodiments, the contact array is a high-density array. The term "high-density contact array" includes at least 12 electrical contacts per 1 centimeter $(cm)^2$ along the surface. In certain embodiments, the high-density contact array may have at least 20 electrical contacts per 1 $cm^2$ or at least 40 electrical contacts per 1 $cm^2$. In more particular embodiments, the high-density contact array may have at least 50 electrical contacts per 1 $cm^2$ or at least 60 electrical contacts per 1 $cm^2$.

In some embodiments, the contact array is positioned within an area that is at most 500 $mm^2$. In certain embodiments, the contact array is positioned within an area that is at most 400 $mm^2$ or at most 300 $mm^2$. The contact array may have a length measured along a centerline that is at least 10 mm. In some embodiments, the length of the contact array is at least 15 mm or at least 20 mm. In certain embodiments, the length of the contact array is at least 25 mm or at least 30 mm. In more particular embodiments, the length of the contact array is at least 40 mm or at least 50 mm. The contact array may have a width measured transverse to the centerline that is at most 40 mm. In some embodiments, the width of the contact array is at most 30 mm or at most 25 mm. In certain embodiments, the width of the contact array is at most 20 mm or at most 15 mm. In more particular embodiments, the width of the contact array is at most 10 mm or at most 7.5 mm.

As used herein, the term "electrical contact" includes a conductive element (e.g., metal) that is electrically coupled to a respective conductive pathway and is configured to engage another contact for establishing an electrical connection. The electrical contacts may include, for example, stamped-and-formed contacts. Electrical contacts may be soldered, welded, or otherwise positioned for electrically coupling to the respective conductive pathways. An electrical contact may include a contact pad provided along a surface of a printed circuit. In some embodiments, the electrical contact includes a movable segment that is configured to be deflected or otherwise moved during a mating operation. For example, electrical contacts may include spring fingers or pogo contacts.

As described herein, the electrical contacts form a contact array that is configured to couple to a corresponding array. Each electrical contact has a fixed location or address with respect to other electrical contacts in the contact array. The contact arrays may be one dimensional (e.g., single row or single column) or at least two-dimensional. More specifically, the electrical contacts may be positioned in a designated manner along at least two dimensions. For example, the electrical contacts may coincide with a plane that extends along or parallel to a centerline of the cable segment. Alternatively, one or more of the electrical contacts may have a different depth or Z-position with respect to other electrical contacts. Accordingly, the contact arrays may be three-dimensional.

As used herein, the term "conductive pathway" includes a pathway that conducts electrical current. In particular embodiments, a conductive pathway transmits data signals. In some embodiments, one or more conductive pathways may conduct electrical power. A conductive pathway may include an insulated wire, a coaxial cable, or a conductive trace of flex circuit. In some embodiments, insulated wires may be arranged in pairs, such as twin-axial (or twinax) cables or twisted pairs. A conductive pathway may also be stamped from sheet metal and then overmolded with a dielectric material. Similarly, a conductive pathway may be ink-printed or screen-printed onto a dielectric material.

As used herein, the term "cable" or "cable segment" includes at least one tubular element that provides a passage for conductive pathways and, optionally, other longitudinal elements (e.g., guidewires or channels for fluid). For example, a cable segment may include an insulated jacket and a shielding layer (e.g., tape) that surrounds insulated wires. A cable segment may include two or more different types of tubular elements that are connected with one another. For instance, a cable segment may include a flexible tube and a rigid shaft that are coupled end-to-end to each other.

As used herein, a "modular device" is a device at or near an end of the catheter assembly that is configured to at least one of detect signals from the surrounding environment or provide therapy to the surrounding environment. In some embodiments, the modular device is an ultrasound device or transducer. For example, the ultrasound device may be or include a piezoelectric micromachined ultrasonic transducer (PMUT) or a capacitive micromachined ultrasonic transducer (CMUT). In some embodiments, the modular device may include or constitute an imaging sensor (e.g., CMOS). In some embodiments, the modular device may include a sensor or detector that observes a designated parameter of the surrounding environment, such as pressure or temperature.

In some embodiments, the modular device may be configured for providing therapy, such as tissue ablation. Ablation may refer to the direct application of chemical or thermal therapies to a designated region of an organ or tissue in an attempt to at least substantially damage or destroy the designated region. For example, the modular device may be configured to ablate tissue through high intensity focused ultrasound (HIFU), radio-frequency (RF), microwaves, laser, or thermal control (e.g., thermal ablation or cryoablation). The modular device may also be configured for stimulation by delivering electrical pulses. It should be understood that the modular device may also be configured for both detection and therapy in some embodiments.

The modular device may generate and/or receive data signals through the conductive pathways of the catheter assembly. Data signals may be processed to obtain designated information, such as images, values of predetermined parameters (e.g., pressure, heat), or information regarding orientation of a modular device, etc. The conductive pathways may also supply electrical power to the modular device.

As used herein, phrases such as "a plurality of [elements]" and "an array of [elements]" and the like, when used in the detailed description and claims, do not necessarily include each and every element that a component may have. The component may have other elements that are similar to the plurality of elements. For example, the phrase "an array of electrical contacts [being/having a recited feature]" does not necessarily mean that each and every electrical contact of a connector has the recited feature. Other electrical contacts may not include the recited feature. Accordingly, unless explicitly stated otherwise (e.g., "each and every electrical contact of the connector [being/having a recited feature]"), embodiments may include similar elements that do not have the recited features.

In order to distinguish similar elements in the detailed description and claims, various labels may be used. For example, an electrical connector may be referred to as a plug connector, a receptacle connector, and/or a mating connector. Electrical contacts may be referred to as plug contacts, receptacle contacts, and/or mating contacts. The contact arrays may be referred to as mating arrays, terminal arrays, and secondary arrays. When similar elements are labeled differently (e.g., plug contacts, receptacle contacts, or mating contacts), the different labels do not necessarily require structural differences.

FIG. 1 is a schematic view of a system 100 formed in accordance with an embodiment. The system 100 may be, for example, an ultrasound system configured to acquire ultrasound data within a patient, a camera system configured to acquire images within a body, or a monitoring system configured to monitor a parameter-of-interest (e.g., temperature or pressure). The system 100 includes a catheter assembly 102 and a control system 104 that are communicatively coupled to one another. In the illustrated embodiment, the control system (or control device) 104 is a portable communication device having a display 106. For example, the control system 104 may be a smartphone, tablet computer, laptop computer, or a similar portable communication device. In other embodiments, the control system 104 may be a desktop computer or workstation.

The control system 104 (or computing system) may include one or more processors (or processing units) that are configured to execute programmed instructions. For example, the control system 104 may receive data signals that are based on external signals detected by the catheter assembly 102, process the data signals, and generate useful information for the user. Optionally, the control system 104 may transform the data signals into images that are shown on the display 106. The display 106 may include a touch screen that is configured to receive user inputs such that a user may control operation of the system 100 through the touch screen. Alternatively or in addition to the touchscreen, the control system 104 may include an input device, such as a keyboard or touchpad, for receiving user inputs. The control system 104 may also be configured to communicatively couple to an external input device, such as a mouse or external keyboard. In some embodiments, the control system 104 may transmit signals to emit energy from a modular device 114 of the catheter assembly 102.

The catheter assembly 102 is configured to be inserted into a body (e.g., human or animal). For example, the catheter assembly 102 may be configured for real-time three-dimensional (3D) ultrasound imaging. Ultrasound can be excited by many different methods, including the piezoelectric effect, magnetostriction, and the photoacoustic effect. The catheter assembly 102 may also be configured to emit energy for delivering therapy, such as tissue ablation.

The catheter assembly 102 includes a cable assembly 108 extending between proximal and distal ends 110, 112 of the cable assembly 108 and having conductive pathways (not shown) extending therebetween. The modular device 114 is coupled to the distal end 112 and is configured to be inserted into a body. The cable assembly 108 includes first and second cable segments 120, 122 that are interconnected by a plug connector 124 and a receptacle connector 126. The first and second cable segments 120, 122 have respective elongated cables 121, 123 and respective conductive pathways 125, 127 extending therethrough. The elongated cables 121, 123 may include one or more layers (e.g., insulated jacket, shielding tape, and the like) that surround the conductive pathways 125, 127, respectively. As shown, the plug connector 124 is coupled to a mating end 190 of the elongated cable 121. The receptacle connector 126 is coupled to a mating end 192 of the elongated cable 123.

Although the cable assembly 108 includes only two cable segments 120, 122, it should be understood that embodiments may include more than two cable segments. In some embodiments, one or more of the cable segments may be disposable. For example, a kit 109 may include the second cable segment 122 and a plurality of first cable segments 120 that are discarded after being inserted into a body. As such, the first cable segment 120 may be referred to as a single-use disposable segment. In other embodiments, however, other cable segments may be disposable or the cable segments may be designed for using with more than one body after the catheter is reprocessed.

In the illustrated embodiment, the first cable segment 120 includes the plug connector 124 and the second cable segment 122 includes the receptacle connector 126. In other embodiments, however, the first cable segment 120 includes the receptacle connector 126 and the second cable segment 122 includes the plug connector 124. The plug connector 124 and the receptacle connector 126 are configured to pluggably engage one another during a mating operation. The plug connector 124 and the receptacle connector 126 may align with one another along a centerline (not shown) of the cable assembly 108. The centerline extends along a center of the cable assembly 108.

During the mating operation, at least a portion of the plug connector 124 may be received within a mating cavity (not shown) of the receptacle connector 126 and/or at least a portion of the receptacle connector 126 may be received within a mating cavity (not shown) of the plug connector 124. As described herein, each of the plug connector 124 and the receptacle connector 126 includes at least one contact array that engages another contact array along a mating zone. The mating zone extends along the centerline. The plug connector 124 and the receptacle connector 126 may form a snug fit. The snug fit may impede egress of a fluid along the mating zone where the contact arrays engage each other.

The first cable segment 120 also includes an operator handle 128. The operator handle 128 may enable a user to control the modular device 114 within the body. For example, the operator handle 128 may enable the user to manipulate (e.g., move or position) the modular device 114 within the body to obtain the designated information or apply the designated therapy.

The modular device 114 is communicatively coupled to the control system 104 through the cable assembly 108. The modular device 114 is sized for insertion into, for example, a patient's body. The modular device 114 may be configured for at least one of detecting signals from the surrounding environment or applying therapy to the surrounding environment. In particular embodiments, the modular device 114 includes a solid state device, such as complementary metal-oxide semiconductors (CMOSs), charge-coupled devices (CCDs), and the like. As one example, the modular device 114 is an ultrasound device or transducer. For example, the ultrasound device may be or include a piezoelectric micromachined ultrasonic transducer (PMUT) or a capacitive micromachined ultrasonic transducer (CMUT). In other embodiments, the modular device 114 may include or constitute an imaging sensor (e.g., CMOS). The modular device 114 may also be a sensor that is configured to measure conditions within a designated space, such as pressure or temperature. The modular device 114 may also be a mapping device, such as an electrophysiology (EP) mapping device. In EP mapping, electrodes (e.g., electrocardiographic ECG electrodes) touch a surface of tissue to detect biometric data.

In some embodiments, the modular device 114 may be configured for providing therapy. Therapy may include tissue ablation or stimulation. Stimulation may include delivering electrical pulses or generating electrical fields that stimulate nerve tissue. Ablation may include direct application of chemical or thermal therapies to a designated region of an organ or tissue in an attempt to at least substantially damage or destroy the designated region. The source of energy used for ablation may be radiofrequency (RF) or high intensity ultrasound (HIFU). The modular device 114 may also be configured for cryoablation. Optionally, the modular device may include one or more flow sensors for detecting fluid that is dispensed or received during ablation.

In some embodiments, the entire system 100 may be configured for insertion into a patient's body. For example, the catheter assembly 102 may include a stimulation device (e.g., neurostimulator or pacemaker) and the control system 104 may be a pulse generator that is configured to provide a designated sequence of electrical pulses to the catheter assembly 102 for delivering the therapy.

The catheter assembly 102, however, may be used for purposes other than medical applications. For example, the modular device 114 may include an imaging sensor (e.g., CMOS) or other type of detector/transducer that detects external signals and communicates the external signals, directly or indirectly, to the control system 104.

Figure 2:
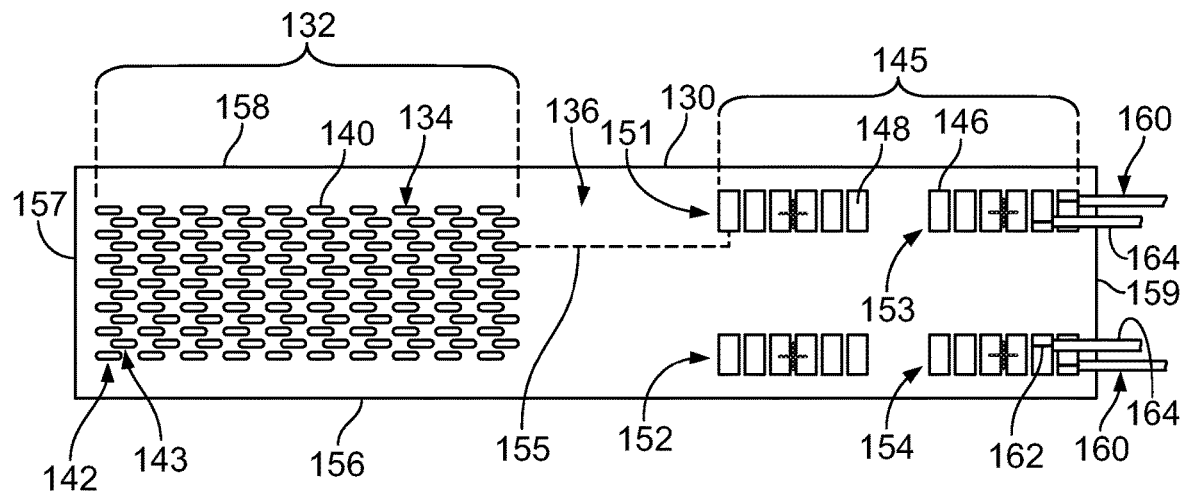
FIG. 2 is a plan view of an array of electrical contacts that may be used with the catheter assembly of FIG. 1.

FIG. 2 is a plan view of a contact array 132 of electrical contacts 134 that may be used with the catheter assembly 102 (FIG. 1). In the illustrated embodiment, the contact array 132 is positioned along a side surface 136 of a printed circuit 130. The printed circuit 130 may be a printed circuit board (PCB) or a flex circuit. The electrical contacts 134 constitute contact pads 140 that are exposed along the side surface. The contact pads 140 are arranged in a series of staggered rows 142, 143 to form a dense contact array. In the illustrated embodiment, the contact array 132 includes at least 100 contact pads 140. In other embodiments, however, the contact array 132 may include fewer or more electrical contacts.

FIG. 2 also illustrates a contact array 145 of electrical contacts 146 that may be used with the catheter assembly 102 (FIG. 1). In the illustrated embodiment, the contact array 145 is also positioned along the side surface 136 of the printed circuit 130. The electrical contacts 146 are contact pads 148 that are exposed along the side surface 136 and have a greater surface area than a surface are of the contact pads 140. The contact pads 148 are arranged in columns 151-154.

The printed circuit 130 has longitudinal edges 156, 158 and distal edges 157, 159. As shown, the printed circuit 130 has an essentially rectangular shape. It should be understood, however, that printed circuits may have a variety of desired shapes. The printed circuit 130 may include conductive traces and vias that electrically connect the electrical contacts 134 and respective electrical contacts 146. An exemplary trace 155 is shown in FIG. 2 and extends between one electrical contact 134 and one electrical contact 146. It should be understood that the printed circuit 130 may have numerous conductive traces and vias for electrically connecting the electrical contacts of the different arrays.

Also shown, conductive pathways 160 have been terminated to select contact pads 148. The conductive pathways 160 may be, for example, wire conductors 162 from insulated wires 164. The wire conductors are mechanically and electrically coupled to the contact pads 148. For example, the wire conductors may be soldered or welded to the contact pads 148. It should be understood that the limited number of conductive pathways 160 shown in FIG. 2 are for illustration only. In practical applications, each and every contact pad 148 may have a conductive pathway 160 terminated thereto.

The printed circuit 130 may be manufactured through known printed circuit board (PCB) technologies. The printed circuit 130 may be a laminate or sandwich structure that includes a plurality of stacked substrate layers. Each substrate layer may include, at least partially, an insulating dielectric material. By way of example, the substrate layers may include a dielectric material (e.g., flame-retardant epoxy-woven glass board (FR4), polyimide, polyimide glass, polyester, epoxy-aramid, and the like); a bonding material (e.g., acrylic adhesive, modified epoxy, phenolic butyral, pressure-sensitive adhesive (PSA), preimpregnated material, and the like); a conductive material that is disposed, deposited, or etched in a predetermined manner; or a combination of the above. The conductive material may be copper (or a copper-alloy), cupro-nickel, silver epoxy, conductive polymer, and the like. It should be understood that substrate layers may include sub-layers of, for example, bonding material, conductive material, and/or dielectric material.

It should be understood, however, that contact arrays may be manufactured through methods other than PCB manufacturing, such as laser direct structuring (LDS), two-shot molding (dielectric with copper traces), and/or ink-printing. Structural components may be manufactured by molding a dielectric material (e.g., thermoplastic) into a designated shape. Conductive elements (e.g., conductors, electrical contacts) may then be disposed on surfaces of the mold through, for example, ink-printing. Alternatively, conductive elements may be first formed and then a dielectric material may be molded around the conductive elements allowing for a portion of the conductive elements (e.g., the electrical contacts) to be exposed. For example, the conductive elements may be stamped from sheet metal, disposed within a cavity, and then surrounded by a thermoplastic material that is injected into the cavity.

Figure 3:
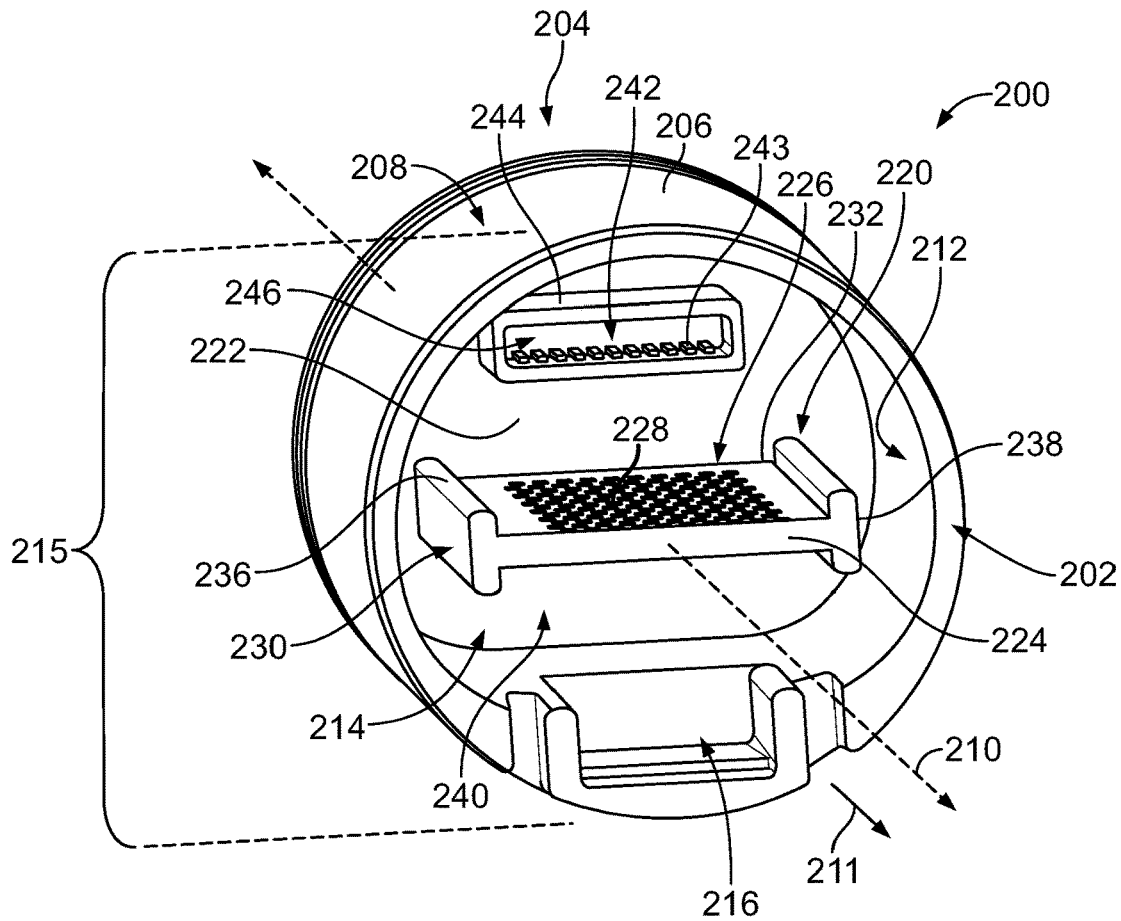
FIG. 3 is a front perspective view of a plug connector formed in accordance with an embodiment that may be used with the catheter assembly of FIG. 1.
Figure 4:
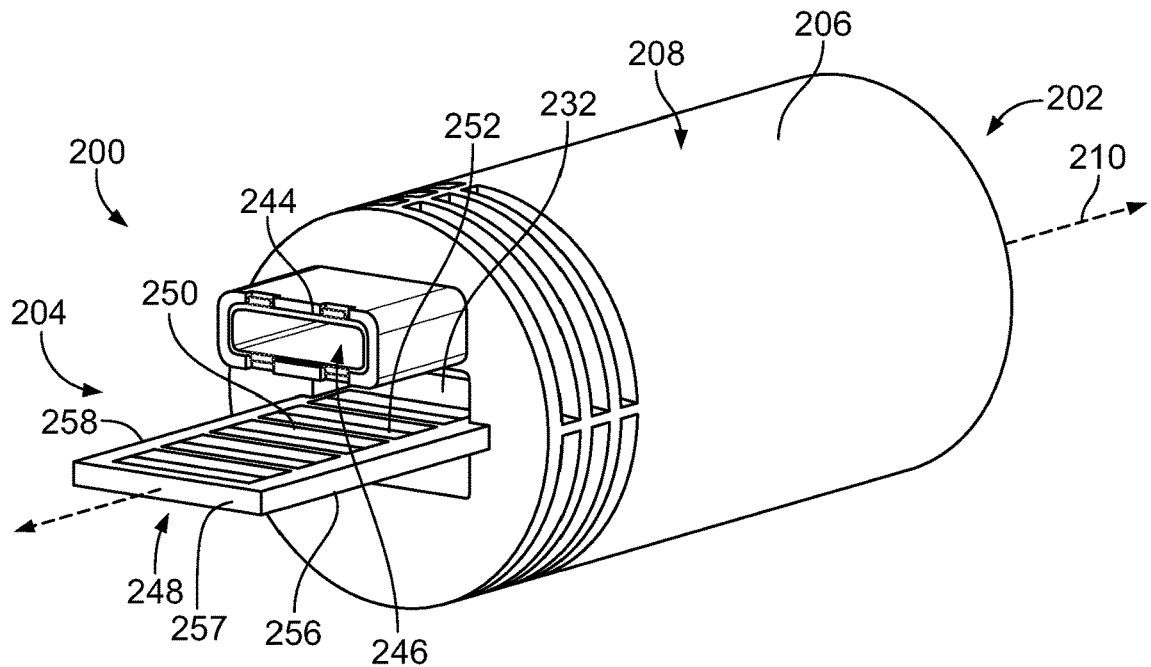
FIG. 4 is a rear perspective view of the plug connector of FIG. 3.

FIG. 3 is a front perspective view of a plug connector 200, and FIG. 4 is a rear perspective view of the plug connector 200. The plug connector 200 may be used with the catheter assembly 102 (FIG. 1) or other catheter assemblies described herein. The plug connector 200 is described with reference to a centerline 210. The centerline 210 represents a center of the catheter assembly and extends lengthwise along the catheter assembly and essentially parallel to the conductive pathways. The centerline 210 is linear through the plug connector 200 in FIGS. 3 and 4. Due to the flexibility of the cable, however, the centerline 210 may not be linear for other portions of the catheter assembly. In other embodiments, the centerline 210 is not linear extending through the plug connector. In such embodiments, the plug connector may form an angle (e.g., right-angle) or have another configuration.

The plug connector 200 has a front or mating end 202 and a back or loading end 204. The front and back ends 202, 204 face in opposite directions with respect to each other. The plug connector 200 includes a plug housing 206. The plug housing 206 has an exterior surface 208. In some embodiments, the exterior surface 208 defines an exterior of the catheter assembly at the plug connector 200 and, as such, an outer diameter 215 of the catheter assembly. In other embodiments, the plug housing 206 may be surrounded by other components such that the exterior surface 208 does not represent an exterior of the catheter assembly.

Figure 6:
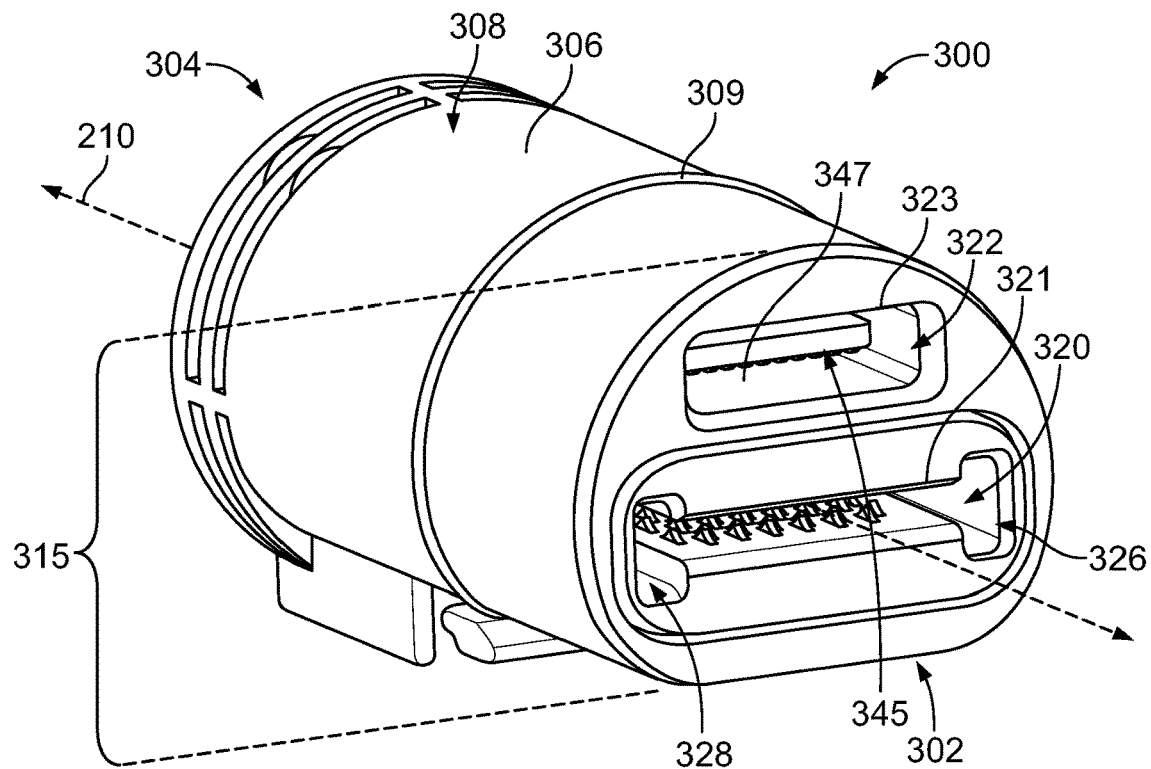
FIG. 6 is a front perspective view of a receptacle connector formed in accordance with an embodiment that may be used with the catheter assembly of FIG. 1.

With respect to FIG. 3, the plug connector 200 also includes an interior wall surface 212. The interior wall surface 212 defines a mating cavity 214 that is sized and shaped to receive at least a portion of another electrical connector, such as the receptacle connector 300 (FIG. 6). The interior wall surface 212 surrounds the centerline 210 and faces radially-inward toward the centerline 210. In the illustrated embodiment, the interior wall surface 212 is essentially smooth for a majority of the interior wall surface 212 having the same radius of curvature. The interior wall surface 212 forms a latch sub-cavity 216.

Also shown in FIG. 3, the plug connector 200 includes a plug substrate 220 that is disposed within the mating cavity 214. The plug substrate 220 projects in an axial direction (e.g., linear direction) along the centerline 210. As used herein, a plug substrate may project or extend along the centerline if a length of the plug substrate coincides with the centerline or if the plug substrate extends parallel to the centerline. The plug substrate 220 extends from an interior base surface 222 to a leading edge 224.

The plug substrate 220 includes a contact array 226 of electrical contacts 228. The contact array 226 is hereinafter referred to as a mating array. The plug substrate 220 may include another contact array 288 (FIG. 9B) of electrical contacts 228 on an opposite side of the plug substrate 220. The contact array 288 is hereinafter referred to as a mating array. The electrical contacts 228 of the mating array 226 may be, for example, contact pads. In the illustrated embodiment, the plug substrate 220 includes a support frame 230 and a printed circuit 232. The printed circuit 232 includes the mating array 226 and has edges (not shown) that are surrounded by the support frame 230. For example, the support frame 230 includes guide walls or ridges 236, 238 that extend parallel to the centerline 210 and along edges of the printed circuit 232. The mating cavity 214 includes a connector-receiving space 240 that is defined between the plug substrate 220 and the interior wall surface 212.

Also shown in FIG. 3, the plug connector 200 includes a secondary array 242. The secondary array 242 is a contact array that includes a plurality of electrical contacts 243. The electrical contacts 243 may be different from the electrical contacts 228. For example, the electrical contacts 243 may be exposed traces or conductors that extend lengthwise through the plug housing 206. The plug connector 200 includes a shield 244 that extends through the plug housing 206. The internal shield 244 defines a secondary channel or passage 246 and surrounds the electrical contacts 243, thereby electrically separating the electrical contacts 243 and the electrical contacts 228.

Figure 5:
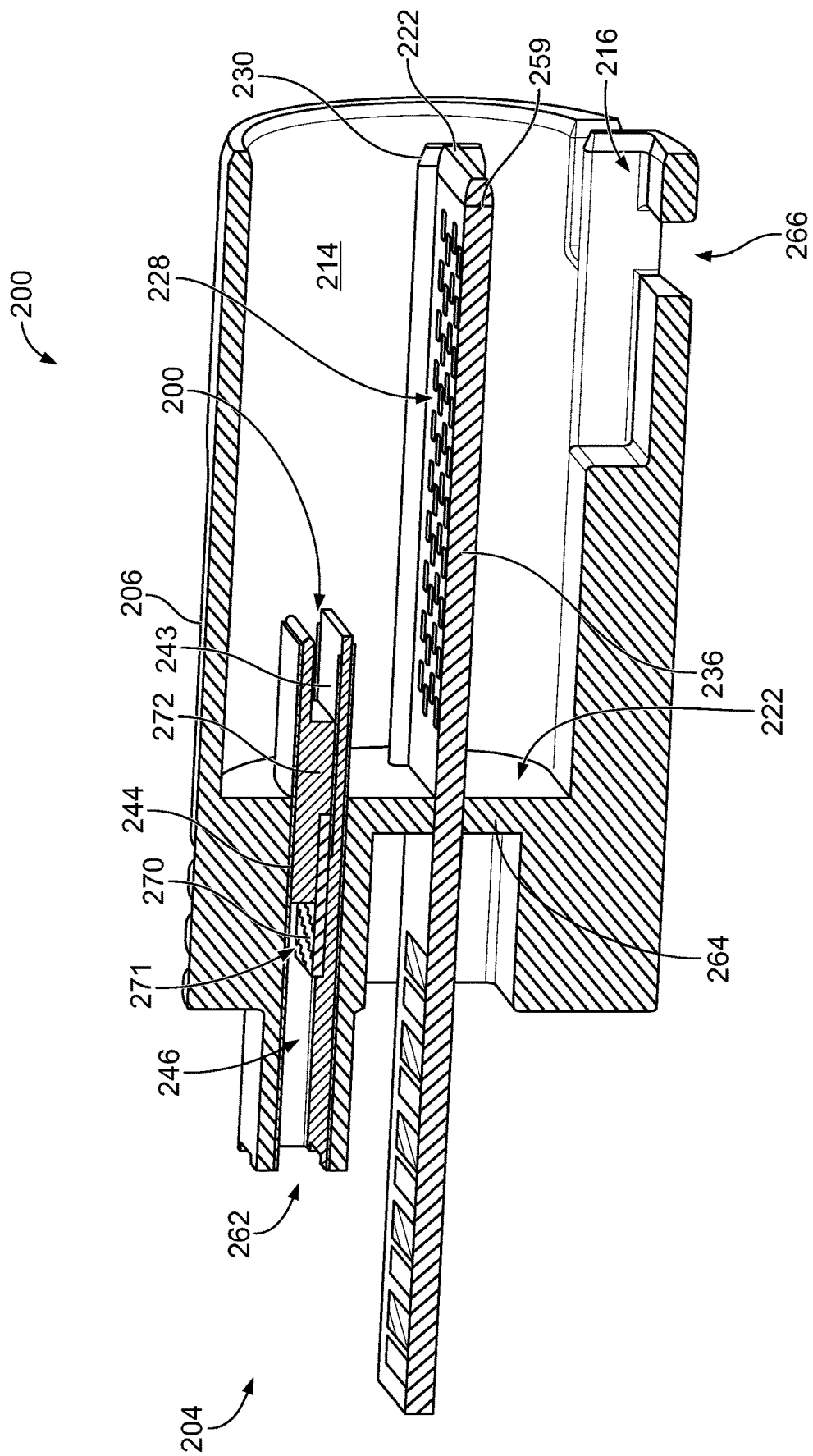
FIG. 5 is a cross-section of the plug connector of FIG. 3.

As shown in FIG. 4, the printed circuit 232 projects in a linear direction away from the plug housing 206. The printed circuit 232 includes longitudinal edges 256, 258, a distal edge 257, and a distal edge 259 (FIG. 5). The longitudinal edges 256, 258 are partially surrounded by the support frame 230 (FIG. 3) along the plug substrate 220 (FIG. 3). A loading section 248 of the printed circuit 232 is exposed and includes a terminal array 250. The terminal array 250 also includes a plurality of electrical contacts 252. The electrical contacts 252 are electrically connected to the electrical contacts 228 (FIG. 3) through conductive traces of the printed circuit 232. The electrical contacts 228 of the mating array 226 (FIG. 3) are coplanar with respect to one another. The electrical contacts 228 are also coplanar with the electrical contacts 252 of the terminal array 250.

Although not shown, the electrical contacts 252 may be mechanically and electrically coupled to conductive pathways of the catheter assembly. For example, ends of insulated wires (not shown) may be stripped to expose wire conductors (not shown). The exposed wire conductors may be soldered or welded to the electrical contacts 252. Also shown in FIG. 4, the internal shield 244 defines an opening to the secondary channel 246.

FIG. 5 is a cross-section of the plug connector 200. As shown, the internal shield 244 extends through the plug housing 206 between first and second openings 260, 262. The first opening 260 opens to the mating cavity 214. The second opening 262 opens to the back end 204. Similarly, the printed circuit 232 extends through a housing wall 264 of the plug housing 206. The housing wall 264 includes the base surface 222. As shown, the leading edge 224 of the plug substrate 220 may be a portion of the support frame 230. The leading edge 224 extends alongside and covers the distal edge 259 of the printed circuit 232. The material of the leading edge 224 may be selected to reduce wear on electrical contacts that engage the leading edge 224, thereby increasing the lifetime of the electrical contacts and/or a number of mating cycles of the connector assembly. The support frame 230 and the housing wall 264 support the printed circuit 232 and hold the printed circuit 232 in a fixed position with respect to the plug housing 206. Also shown, the plug housing 206 forms a latch opening 266 that provides access to the latch sub-cavity 216.

In some embodiments, a printed circuit 270 is positioned within the secondary channel 246 and includes electrical contacts 271. The electrical contacts 271 are conductive traces of the printed circuit 270. The electrical contacts 243 are linear conductors that are terminated to the electrical contacts 271 of the printed circuit 270 and extend through a channel portion 272 of the plug housing 206.

Accordingly, the electrical contacts 228, 243 accessible through the front end 202 are electrically connected to the electrical contacts 252, 271 accessible through the back end 204. Moreover, the mating cavity 214 is physically separated from space at the back end 204 by the housing wall 264. As illustrated by the cross-section of the plug housing 206, the plug housing 206 may be overmolded. For example, the internal shield 244, the printed circuit 232, and the printed circuit 270 may be positioned within a chamber of a mold. A dielectric material may be injected into the chamber and permitted to flow around the internal shield 244, the printed circuit 232, and the printed circuit 270, thereby forming the plug housing 206.

Figure 7:
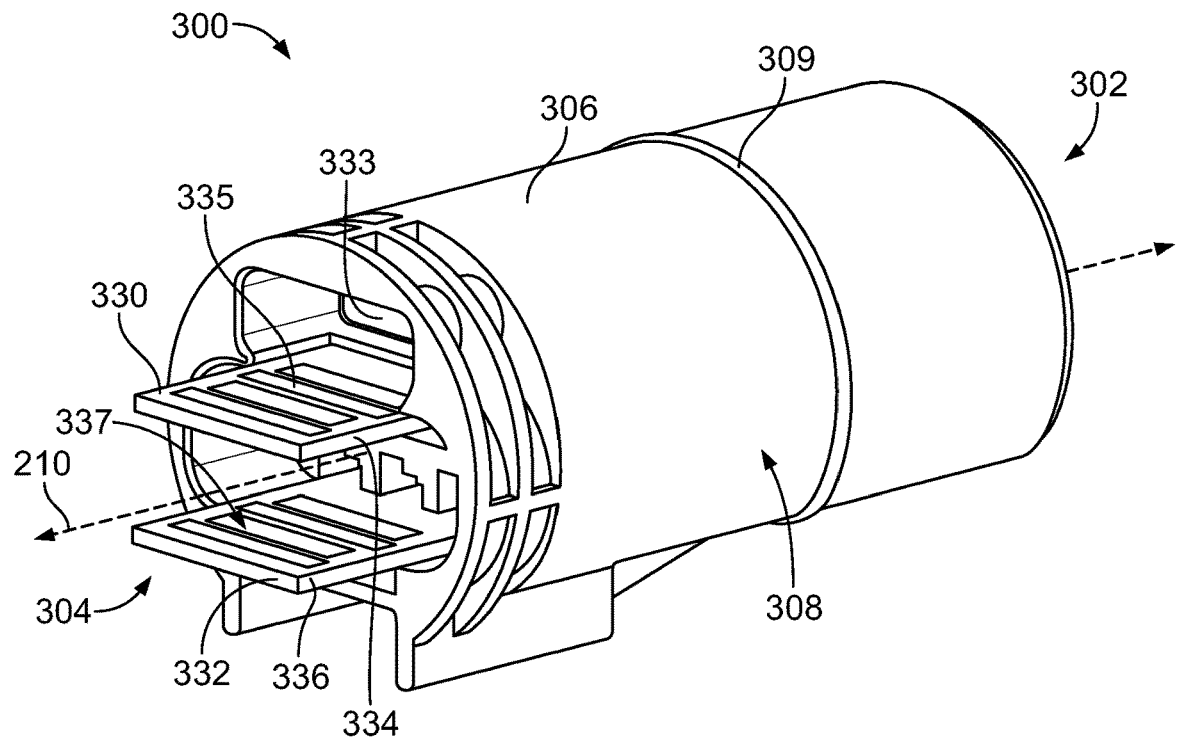
FIG. 7 is a rear perspective view of the receptacle connector of FIG. 6.

FIGS. 6 and 7 are front perspective and rear perspective views of the receptacle connector 300, which is configured to pluggably engage the plug connector 200 (FIG. 3) during a mating operation. For reference, the centerline 210 extends through a center of the receptacle connector 300. The receptacle connector 300 has a front or mating end 302 and a back or loading end 304. The front and back ends 302, 304 face in opposite directions with respect to each other. The receptacle connector 300 includes a receptacle housing 306. The receptacle housing 306 has an exterior surface 308. In some embodiments, the exterior surface 308 defines an exterior of the catheter assembly at the receptacle connector 300 and, as such, an outer diameter 315 of the catheter assembly. In other embodiments, the receptacle housing 306 may be surrounded by other components such that the exterior surface 308 does not represent an exterior of the catheter assembly.

Also shown, the receptacle connector 300 includes a sealing member 309 (e.g., o-ring) that surrounds the exterior surface 308. In some embodiments, the exterior surface 308 is sized and shaped to be inserted into the mating cavity 214 (FIG. 3) of the plug connector 200 (FIG. 3) during a mating operation. The exterior surface 308 may interface with the interior wall surface 212 (FIG. 3) that defines the mating cavity 214 and form a snug fit. The sealing member 309 may engage the interior wall surface 212.

With respect to FIG. 6, the front end 302 includes openings 321, 323 to enclosed slots 320, 322, respectively. More specifically, the enclosed slots 320, 322 are sized and shaped to receive the plug substrate 220 (FIG. 3) and the internal shield 244 (FIG. 3), respectively. The enclosed slot 322 includes a secondary array 345 that is similar to the secondary array 242 (FIG. 3). The secondary array 345 is surrounded by an internal shield 347. The internal shield 347 may electrically separate the conductive pathways through the secondary arrays 242, 345 from other conductive pathways through the mated plug and receptacle connectors 200, 300. The enclosed slot 320 includes guide channels 326, 328 that are configured to receive the guide walls 236, 238, respectively (FIG. 3). Interior surfaces that define the guide channels 326, 328 engage the guide walls 236, 238 to position the plug substrate 220 during the mating operation.

With respect to FIG. 7, the receptacle connector 300 includes first and second printed circuits 330, 332 and the internal shield 347 that are accessible through the back end 304. The first and second printed circuits 330, 332 include terminal sections 334, 336, respectively, that each include terminal arrays 335, 337. The terminal sections 334, 336 represent portions of the printed circuits that will be mechanically and electrically coupled to conducive pathways of the cable assembly (not shown).

Figure 8A:
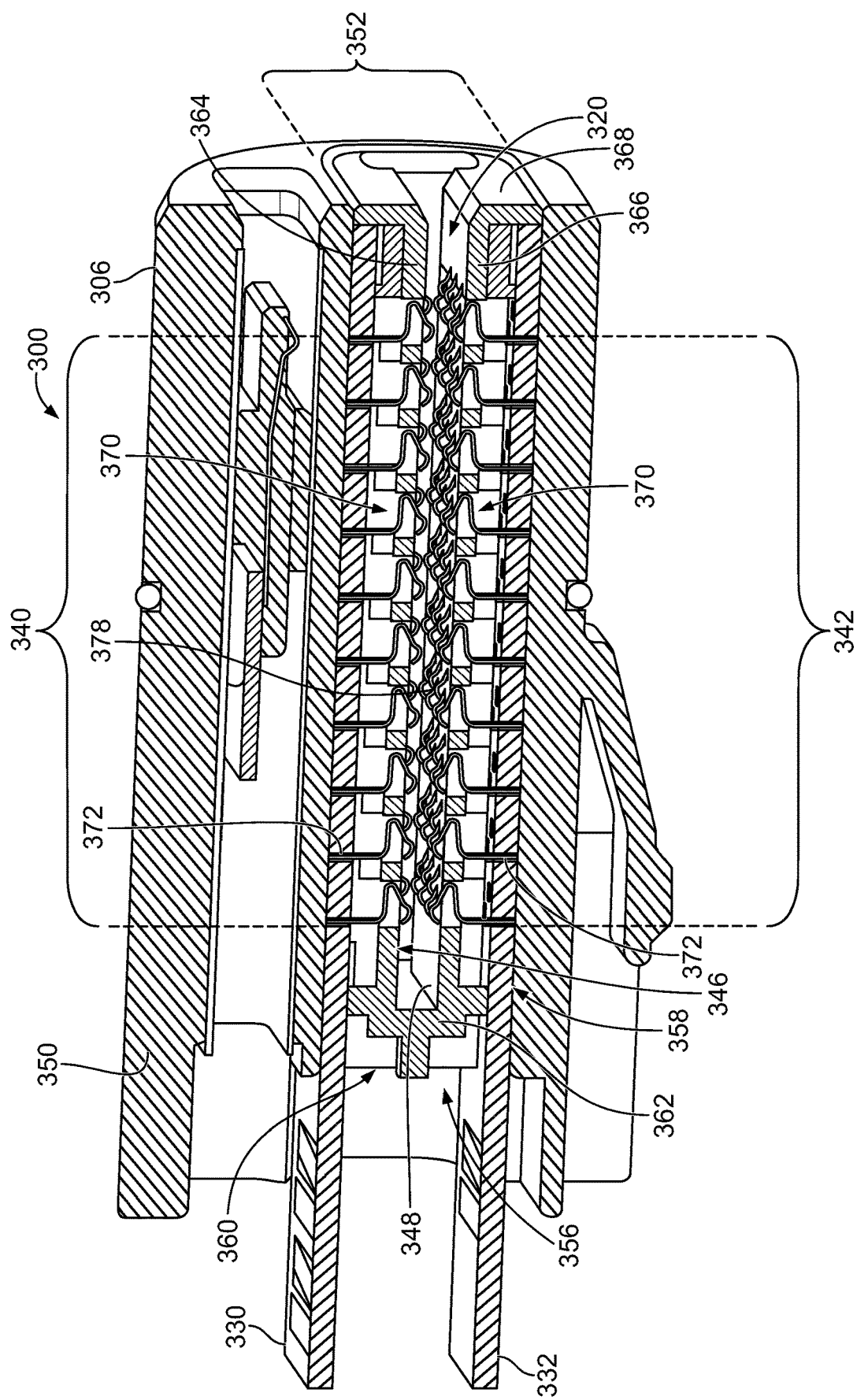
FIG. 8A is a cross-section of the receptacle connector of FIG. 6.

FIG. 8A is a cross-section of the receptacle connector 300. In some embodiments, the receptacle housing 306 includes an outer portion 350 and an inner portion 352 that is disposed within a housing channel 356 of the outer portion 350. The receptacle connector 300 may include a circuit sub-assembly 358 is positioned within the housing channel 356. The circuit sub-assembly 358 includes a carrier 360 having a spacer wall 362, longitudinal walls 364, 366, and a front flange 368. The longitudinal walls 364, 366 include contact openings 370.

In some embodiments, the carrier 360 is a single molded piece. In other embodiments, one or more of the spacer wall 362, the longitudinal walls 364, 366, and the front flange 368 are discrete parts.

Figure 8B:
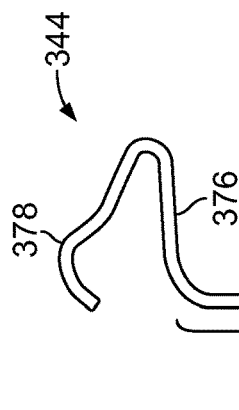
FIG. 8B is a side view of an electrical contact that may be used with the receptacle connector of FIG. 6.

As shown, the first and second printed circuits 330, 332 include system arrays 340, 342, respectively. The system arrays 340, 342 include electrical contacts 344. With reference to FIG. 8B, the electrical contact 344 includes a terminating section 374, an intermediate section 376, and a mating segment 378. The mating segment 378 is configured to be deflected during a mating operation.

Returning to FIG. 8A, the electrical contacts 344 are electrically connected to plated thru-holes (PTHs) 372 of the first and second printed circuits 330, 332. The circuit sub-assembly 358 may be assembled by positioning the carrier 360 between the first and second printed circuits 330, 332. The electrical contacts 344 may be inserted through respective contact openings 370 of the longitudinal walls 364, 366. As such, the circuit sub-assembly 358 forms a sandwich-like structure with the carrier 360 disposed between the first and second printed circuits 330, 332. The circuit sub-assembly 358 may be inserted, as a unit, into the housing channel 356. As shown, the front flange 368 may be positioned essentially flush with a front surface of the receptacle housing 306.

The enclosed slot 320 is defined by interior slot surfaces 346, 348 that oppose each other with the enclosed slot 320 therebetween. The longitudinal walls 364, 366 include the interior slot surfaces 346, 348, respectively. As shown, the electrical contacts 344 extend beyond (or clear) the corresponding interior slot surface 346, 348 such that the mating segments 378 are positioned within the enclosed slot 320. The mating segments 378 are shaped to be deflected by the plug substrate 220 (FIG. 3) as the plug substrate 220 is advanced into the enclosed slot 320. For example, the mating segments 378 may be spring fingers that are deflected back toward the corresponding interior slot surface.

Figure 9A:
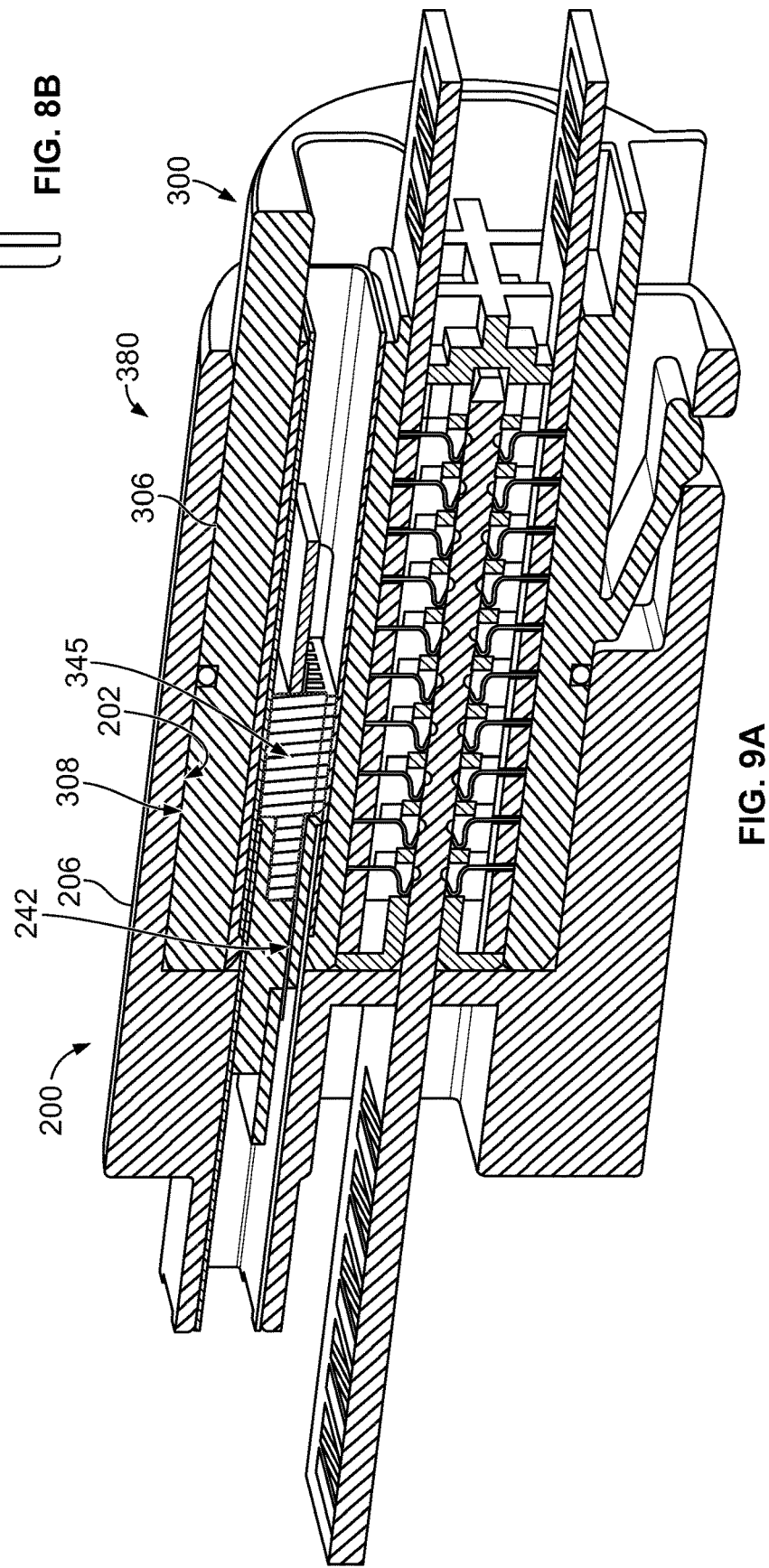
FIG. 9A is a cross-section of a catheter connector assembly that includes the plug connector of FIG. 3 and the receptacle connector of FIG. 6.

FIG. 9A is a cross-section of a catheter connector assembly 380 that includes the plug connector 200 and the receptacle connector 300. In FIG. 9, the plug connector 200 and the receptacle connector 300 are fully mated and form a pluggable engagement. The interior wall surface 212 of the plug housing 206 frictionally engages the exterior surface 308 of the receptacle housing 306. The plug substrate 220 is positioned within the enclosed slot 320 and the electrical contacts 344 are engaged to the electrical contacts 228 (FIG. 3) of the plug substrate 220. Also shown, the secondary array 242 is engaged with the secondary array 345.

Figure 9B:
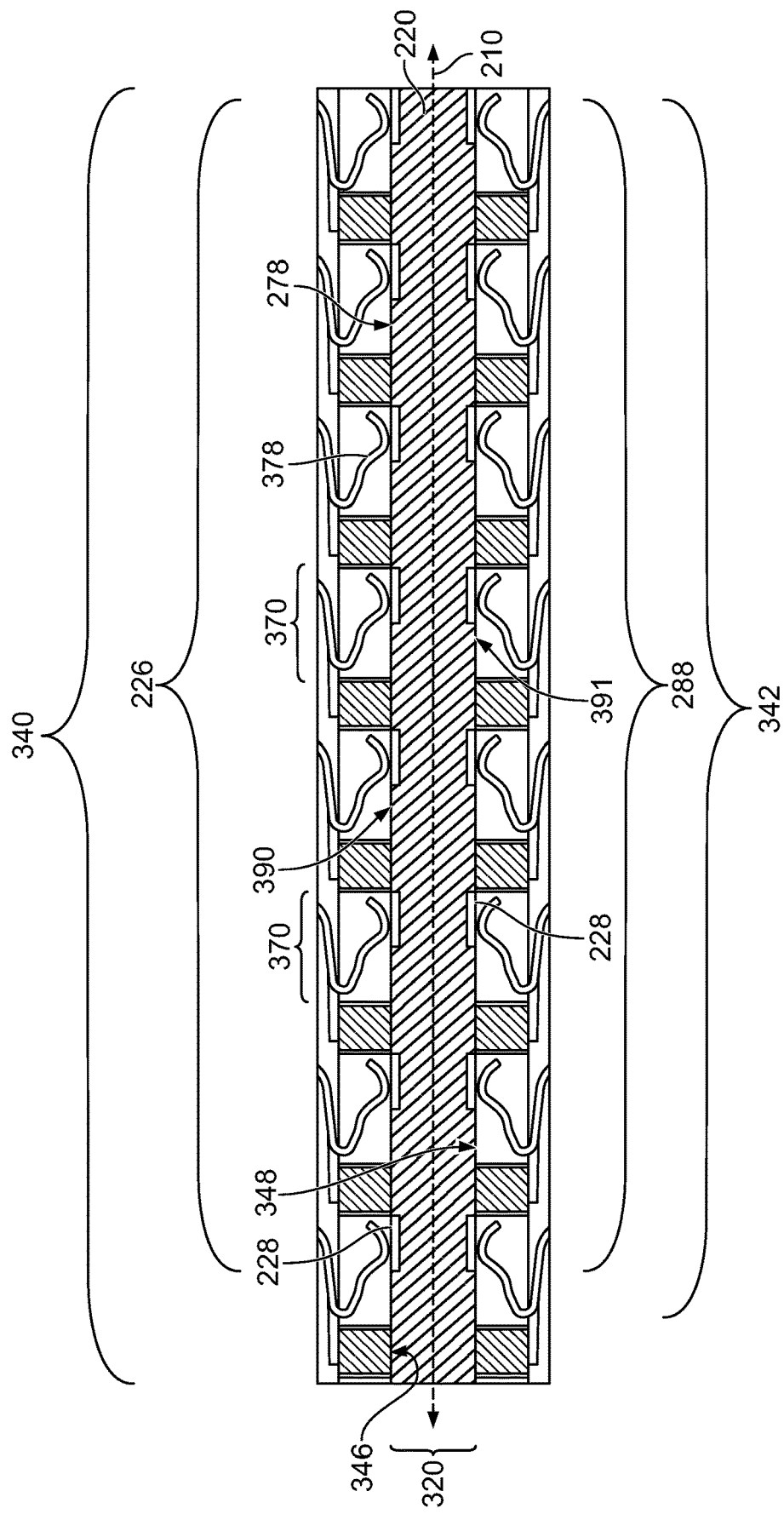
FIG. 9B is an enlarged cross-section of mating zones between the contact arrays of the plug connector and the receptacle connector.

FIG. 9B is an enlarged cross-section of the plug substrate 220 and the system arrays 340, 342 when the plug connector 200 and the receptacle connector 300 are fully mated. The enclosed slot 320 is defined by an interior slot surfaces 346, 348. The mating segments 378 are configured to clear the corresponding interior slot surface. During the mating operation, the mating segments 378 are deflected toward the corresponding interior slot surface and slide along a substrate surface 278 of the plug substrate 220. For example, the mating segments 378 corresponding to the system array 340 are deflected toward the interior slot surface 346, and the mating segments 378 corresponding to the system array 342 are deflected toward the interior slot surface 348. In the illustrated embodiment, each of the mating segments 378 is deflected such that the mating segment 378 is disposed within the corresponding contact opening 370. In the fully mated position, the mating segments 378 engage respective electrical contacts 228 of the plug substrate 220.

As such, the system array 340 and the mating array 226 engage each other along a mating zone 390. The system array 342 and the mating array 288 engage each other along a mating zone 391. Each of the mating zones 390, 391 is within the enclosed slot 320. The mating zones 390, 391 represent areas where the electrical contacts of the system arrays 340, 342, respectively, and the engage the mating arrays 226, 288, respectively, engage one another. The mating zones 390, 391 extend essentially parallel to the centerline 210.

Figure 10:
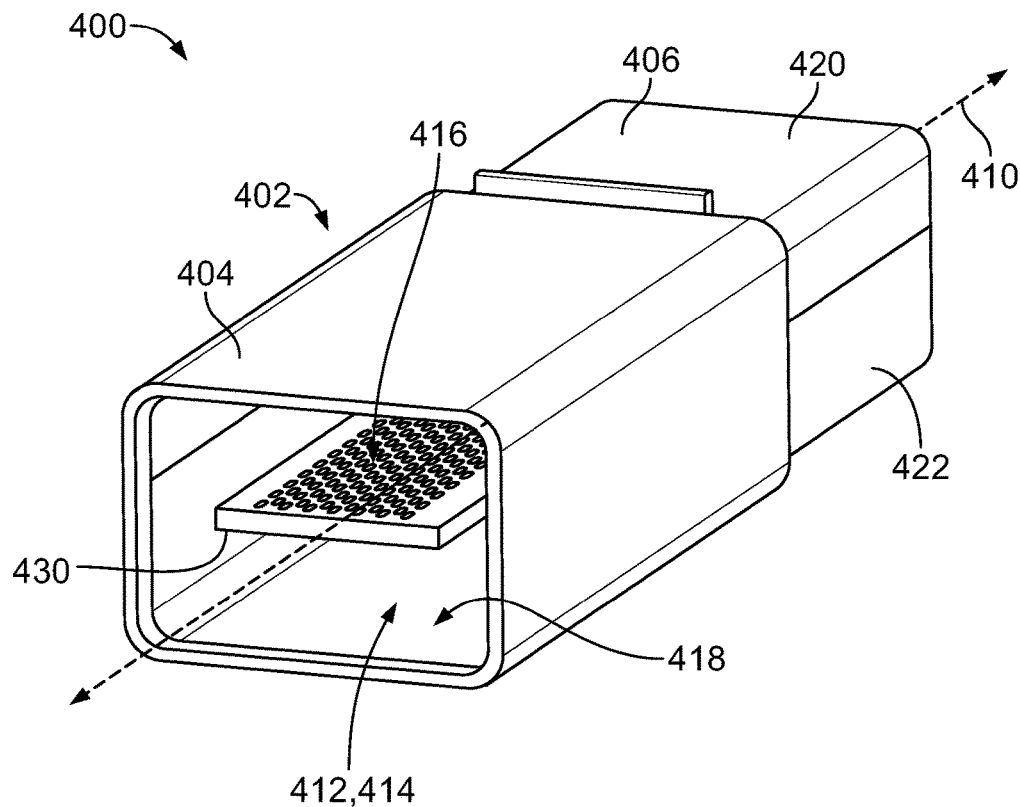
FIG. 10 is a front perspective view of a plug connector formed in accordance with an embodiment that may be used with the catheter assembly of FIG. 1.
Figure 11:
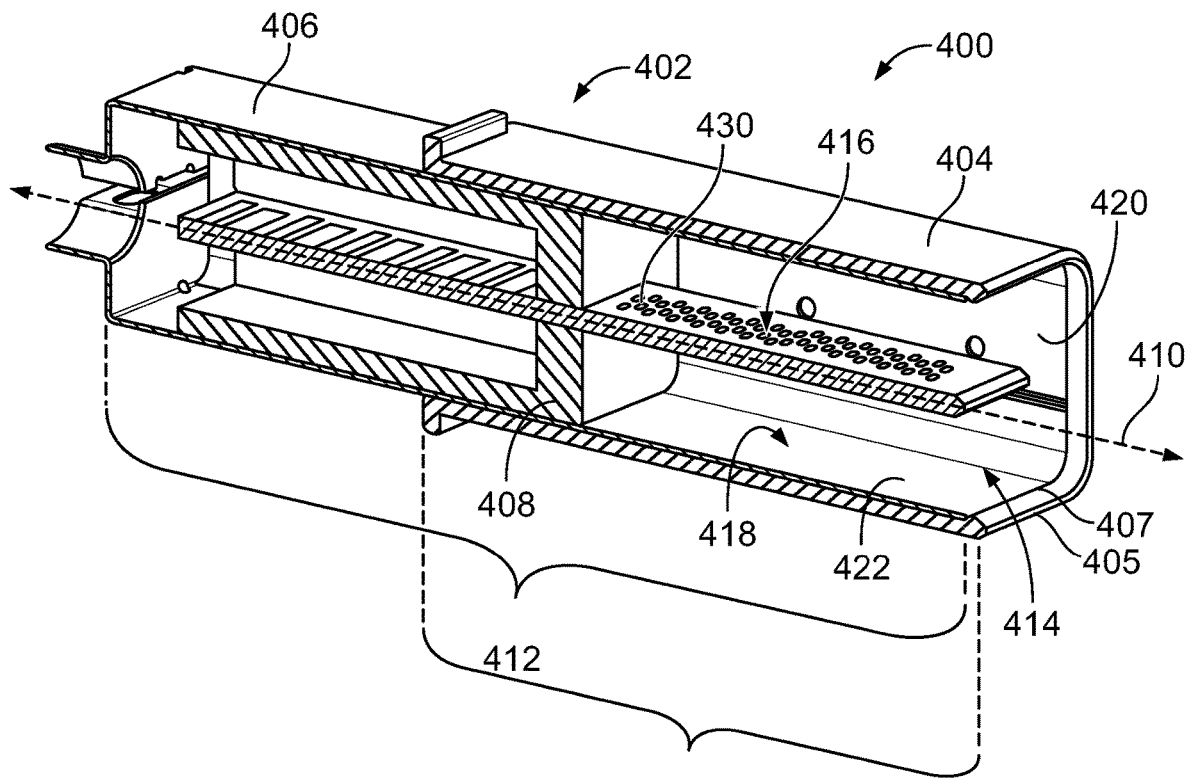
FIG. 11 is a cross-section of the plug connector of FIG. 10.

FIG. 10 illustrates a front perspective view of a plug connector 400, and FIG. 11 is a cross-section of the plug connector 400. The plug connector 400 may form part of a catheter connector assembly and be used with a catheter assembly, such as the catheter assembly 102. The plug connector 400 includes a plug housing 402 and an elongated plug substrate 430 coupled to the plug housing 402. The plug housing 402 includes a connector shroud 404, a connector shield 406, and an interior housing portion 408 (FIG. 11) that are arranged concentric with one another and with respect to a centerline 410. The plug substrate 430 is a printed circuit (e.g., PCB) that extends along the centerline 410. The connector shroud 404 and the housing portion 408 define a mating cavity 414 in which a contact array 416 of the plug substrate 430. The connector shroud 404 includes an interior wall surface 418 that defines the mating cavity 414 and surrounds the centerline 410. The contact array 416 may be referred to as a mating array.

To assemble the plug connector 400, the plug substrate 430 may be molded with or secured to the interior housing portion 408. The interior housing portion 408 and the plug substrate 430 may be inserted into a connector passage 412 defined by the connector shield 406. The mating cavity 414 forms a portion of the connector passage 412 in FIGS. 10 and 11. Optionally, the connector shield 406 includes first and second housing shells 420, 422. The first and second housing shells 420, 422 may be coupled to each other to form the connector passage 412. In such embodiments, the interior housing portion 408 and the plug substrate 430 may be positioned between the first and second housing shells 420, 422 during assembly.

With respect to FIG. 11, the connector shroud 404 includes a shroud passage 424. The connector shield 406 having the plug substrate 430 and the interior housing portion 408 disposed therein may then be inserted into the shroud passage 424. A front edge 407 of the connector shield 406 may substantially align with a front edge 405 of the connector shroud 404. When fully assembled, the plug substrate 430 projects in an axial direction from the housing portion 408 along the centerline 410.

Also shown in FIG. 11, the connector shield 406 includes a strain-relief portion 432. The strain-relief portion 432 defines a loading passage 434 that is sized and shaped to receive conductive pathways and, optionally, other longitudinal elements (e.g., lumen).

Figure 12:
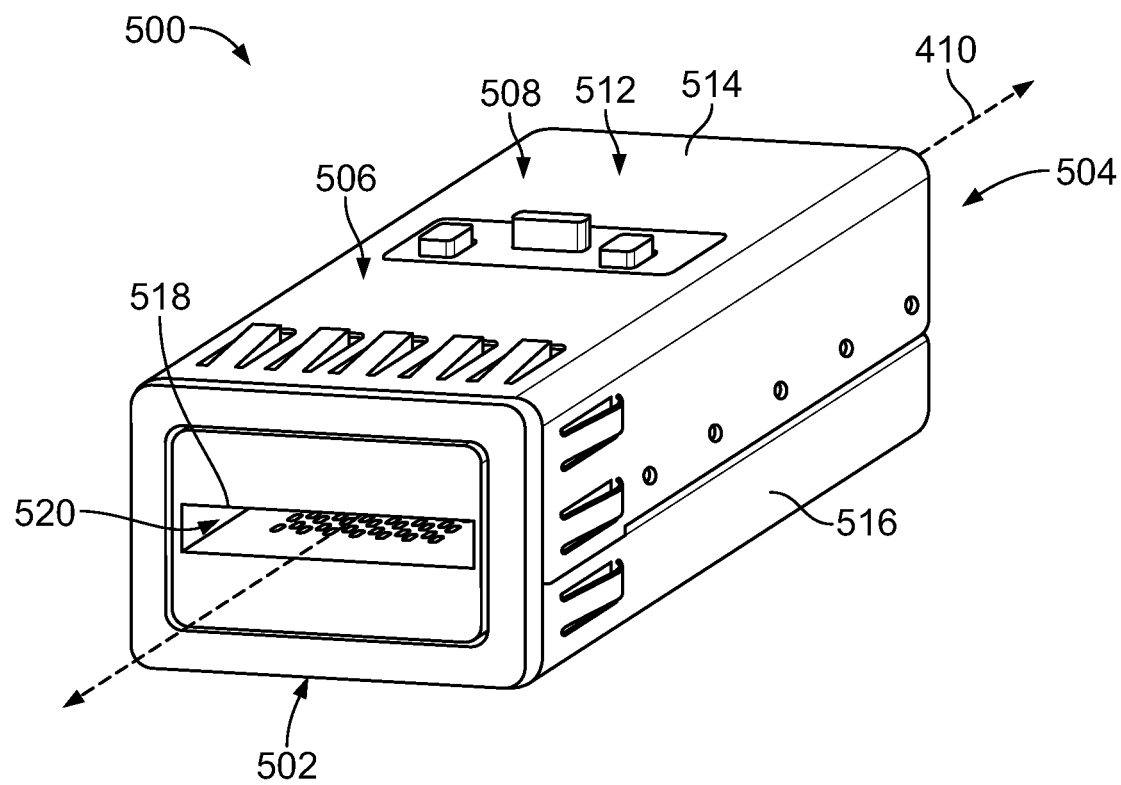
FIG. 12 is a front perspective view of a receptacle connector formed in accordance with an embodiment that may be used with the catheter assembly of FIG. 1.
Figure 13:
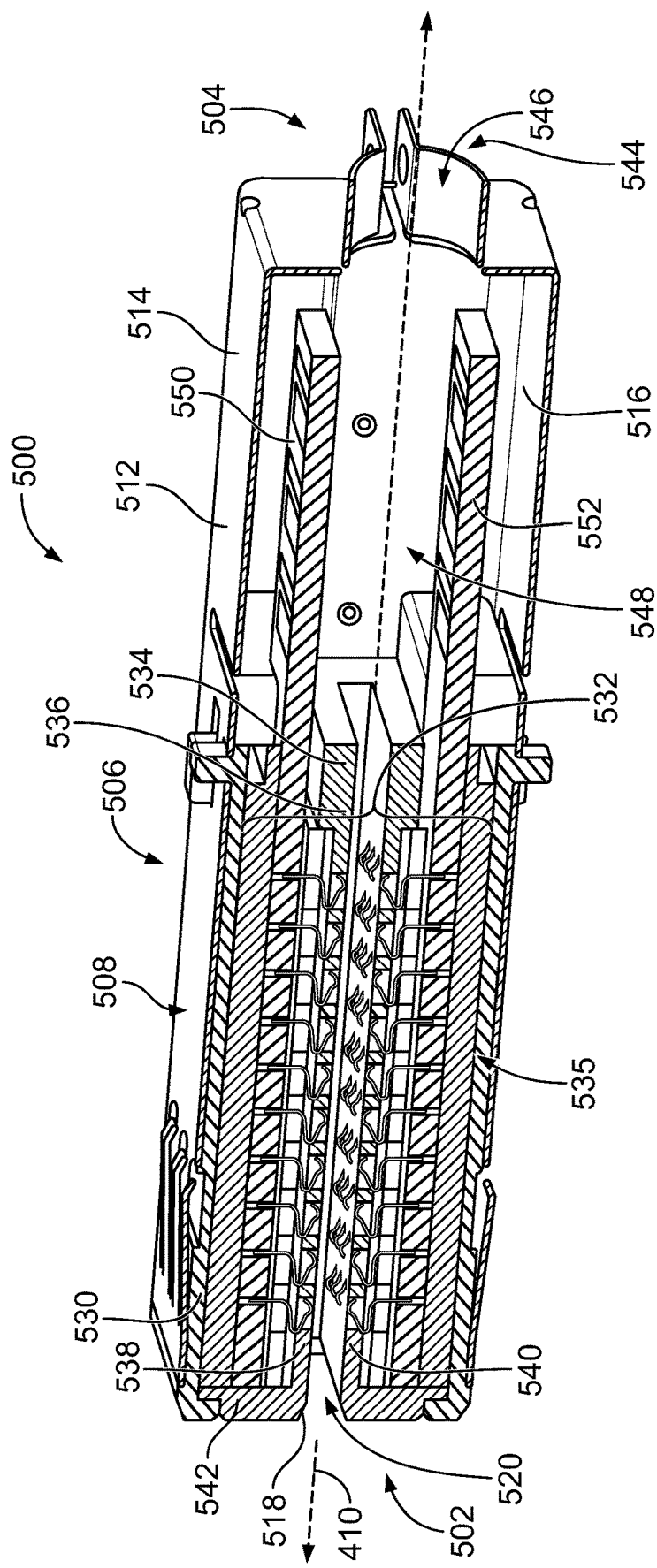
FIG. 13 is a cross-section of the receptacle connector of FIG. 12.

FIG. 12 is a front perspective view of a receptacle connector 500 formed in accordance with an embodiment that may be used with the catheter assembly 102 (FIG. 2) and pluggably engage the plug connector 400 (FIG. 10). FIG. 13 is a cross-section of the receptacle connector 500. For reference, the centerline 410 of the catheter assembly extends through a center of the receptacle connector 500. The receptacle connector 500 has a front or mating end 502 and a back or loading end 504. The front and back ends 502, 504 face in opposite directions with respect to each other. The receptacle connector 500 includes a receptacle housing 506. The receptacle housing 506 has an exterior surface 508. In some embodiments, the exterior surface 508 defines an exterior of the catheter assembly at the receptacle connector 500. The exterior surface 508 defines a cross-sectional profile taken perpendicular to the centerline 410. The cross-sectional profile of the receptacle connector 500 is essentially rectangular in FIGS. 12 and 13.

With respect to FIGS. 12 and 13, the front end 502 includes a slot opening 518 to an enclosed slot 520. More specifically, the enclosed slot 520 is sized and shaped to receive the plug substrate 430 (FIG. 10). The receptacle housing 506 also includes a connector shield 512. In the illustrated embodiment, the connector shield 512 includes first and second housing shells 514, 516 that are stamped-and-formed from sheet metal.

As shown in FIG. 13, the receptacle housing 506 also includes an outer portion 530 having a housing channel 532 and a carrier 534 that is disposed within a housing channel 532 of the outer portion 530. The receptacle connector 500 may include a circuit sub-assembly 535 that is positioned within the housing channel 532. Similar to the circuit sub-assembly 358 (FIG. 8A), the circuit sub-assembly 535 includes the carrier 534 having a spacer wall 536, longitudinal walls 538, 540, and a front flange 542.

Also shown, the receptacle connector 500 includes first and second printed circuits 550, 552. The connector shield 512 includes a strain-relief portion 544. The strain-relief portion 544 defines a loading passage 546 that is sized and shaped to receive conductive pathways and, optionally, other longitudinal elements (e.g., lumen). The loading passage 546 provides access to a terminating space 548. Conductive pathways may extend through the loading passage 546 and into the terminating space 548. The conductive pathways may be terminated to the first and second printed circuits 550, 552.

Figure 14A:
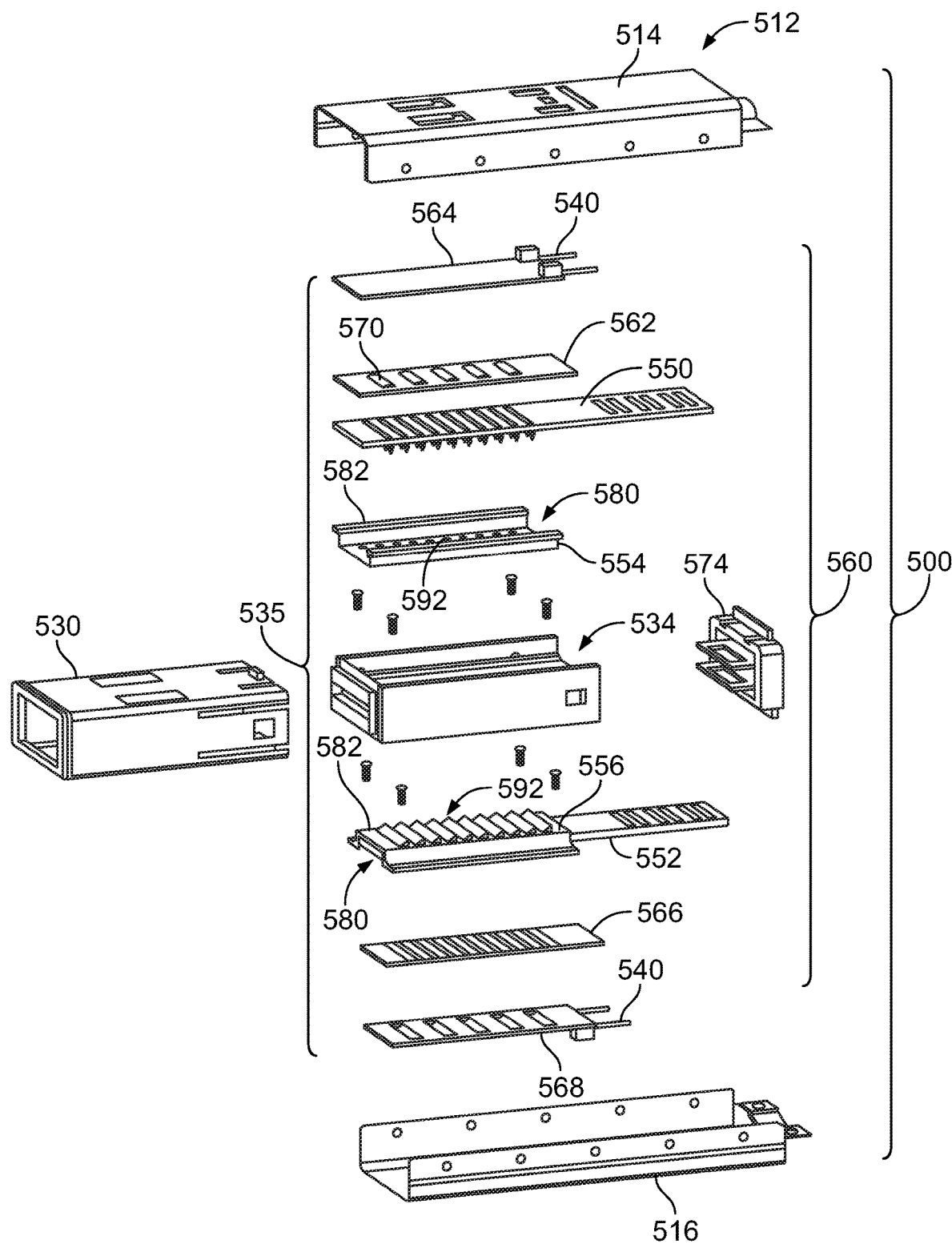
FIG. 14A is an exploded view of the receptacle connector of FIG. 12.
Figure 14B:
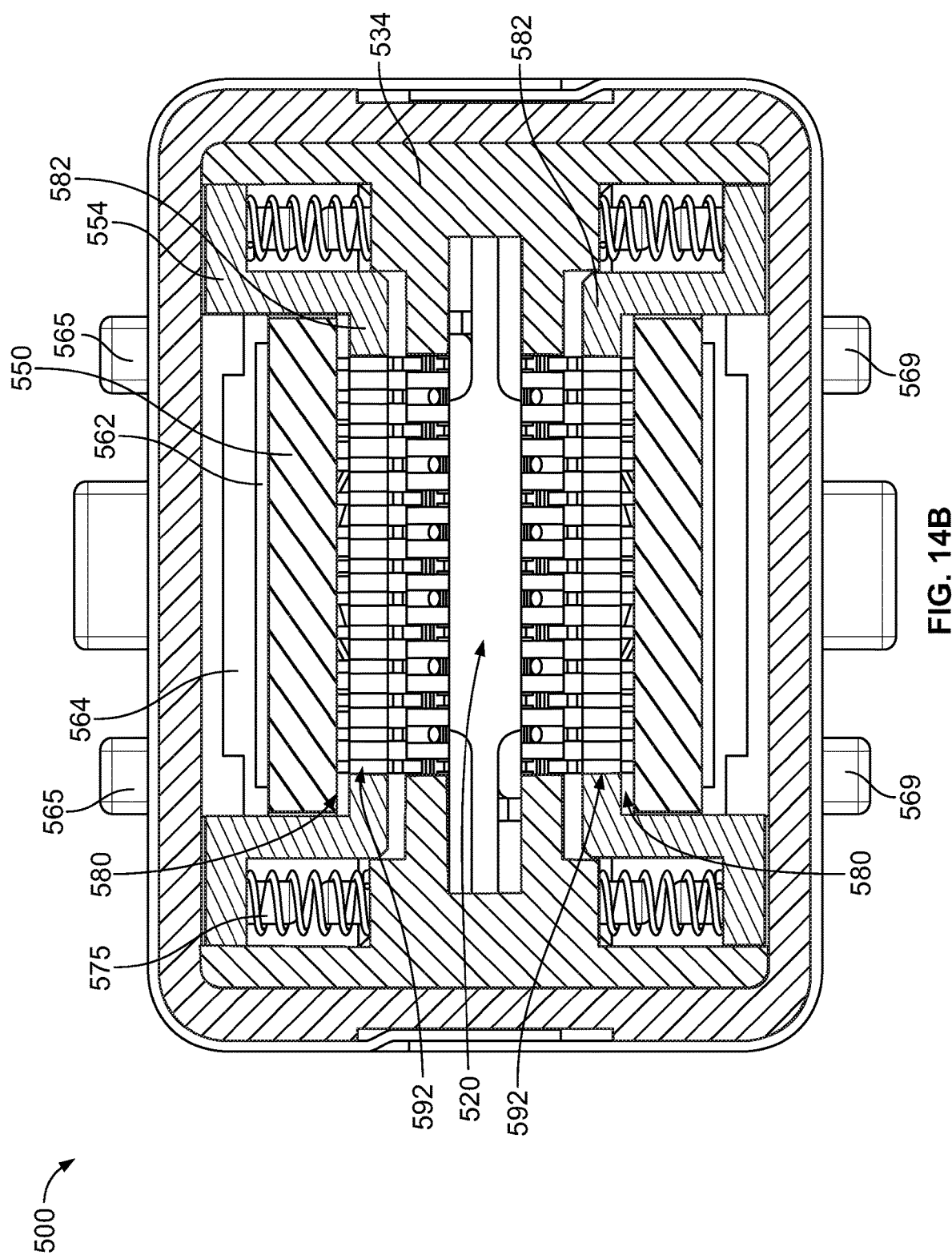
FIG. 14B is a cross-section of the receptacle connector of FIG. 12 taken perpendicular to the centerline.
Figure 14C:
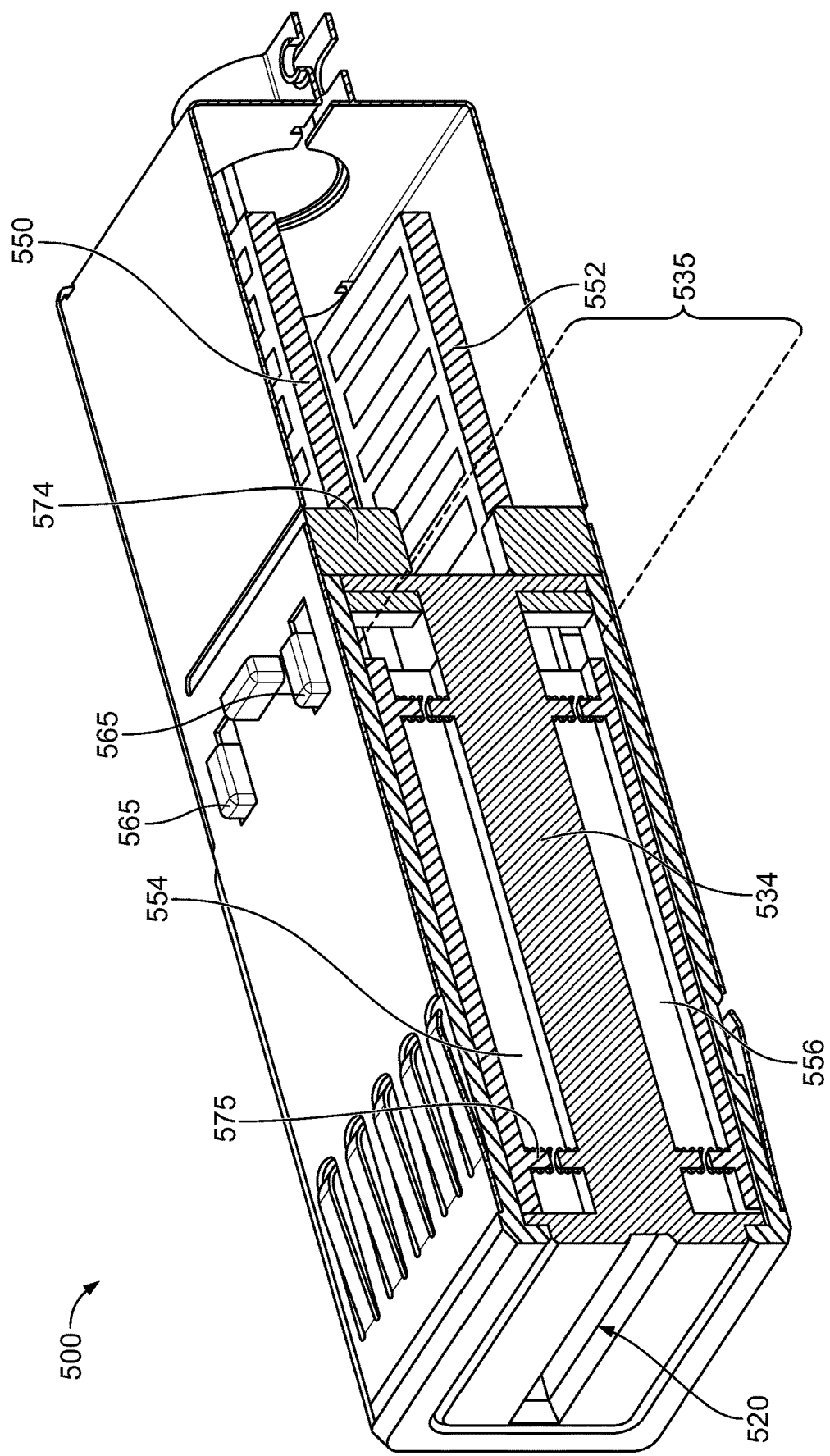
FIG. 14C is a cross-section of the receptacle connector of FIG. 12 taken parallel to the centerline.
Figure 14D:
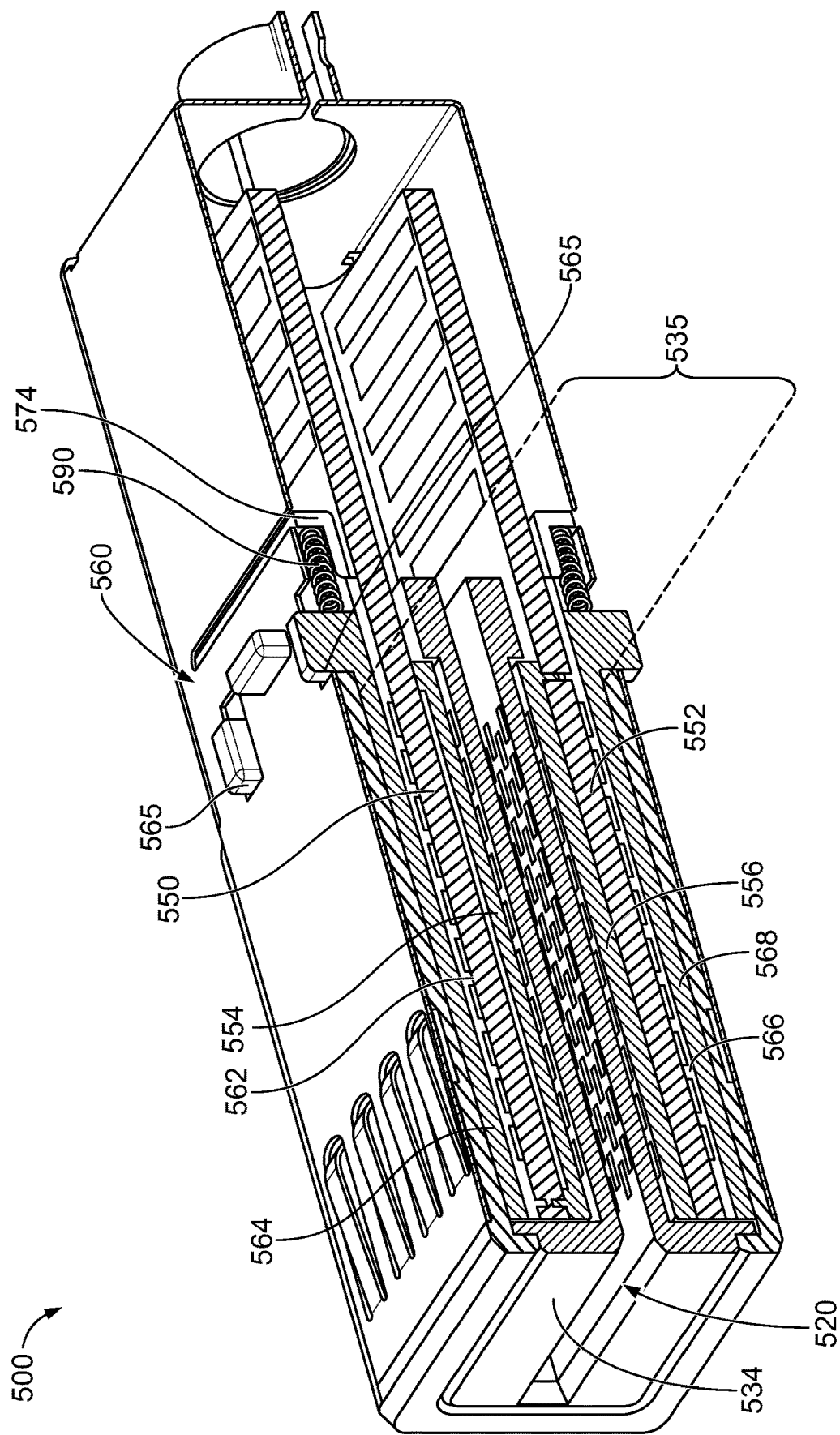
FIG. 14D is a cross-section of the receptacle connector of FIG. 12 taken parallel to the centerline.

FIG. 14A is an exploded view of the receptacle connector 500. FIGS. 14B-14D illustrate different cross-sections of the receptacle connector 500 after being assembled. The circuit sub-assembly 535 includes the carrier 534, the first and second printed circuits 550, 552, first and second trays 554, 556. The circuit sub-assembly 535 also includes a mating mechanism 560. The mating mechanism 560 is configured to move the first and second printed circuits 550, 552 toward the enclosed slot 520 (FIG. 13). The mating mechanism 560 includes a first cam plate 562, a first actuator 564, a second cam plate 566, and a second actuator 568. The first cam plate 562 is positioned side-by-side and forms a slidable interface with the first actuator 564. More specifically, the first cam plate 562 includes ramps 570. The first actuator 564 includes recesses 572 (FIG. 15A, 15B) that receive the ramps 570. The second cam plate 566 is positioned side-by-side and forms a slidable interface with the second actuator 568 in a same or similar manner as the first cam plate 562 and the first actuator 564.

Each of first and second actuators 564, 568 is operably coupled to a respective backstop portion 574. The backstop portions 574 are configured to be positioned within a connector passage 576 (FIG. 15A) defined by the connector shield 512. The backstop portions 574 may engage an end of the carrier 534. The first and second actuators 564, 568 may include biasing members 590 (e.g., coil springs) that are configured to move the first and second actuators 564, 568 away from the backstop portion 574. The first and second actuators 564, 568 also include respective engagement surfaces 565, 569. In the illustrated embodiment, the engagement surfaces 565, 569 extend into an exterior of the receptacle connector 500. In other embodiments, however, the engagement surfaces 565, 569 may be positioned within an interior of the receptacle connector 500, such as within the enclosed slot 520. The engagement surfaces 565, 569 are configured to engage the plug connector 400. In the illustrated embodiment, the engagement surfaces 565, 569 are surfaces of respective bosses or projections.

Each of the first and second trays 554, 556 includes a respective recess 580 for receiving the corresponding printed circuit. The recess 580 is partially defined by a separator wall 582. The separator wall 582 includes an array of contact openings 592 for receiving corresponding electrical contacts. After the circuit sub-assembly 535 is assembled, the circuit sub-assembly 535 may be positioned within the outer portion 530 of the receptacle housing 506. The first and second housing shells 514, 516 may surround the outer portion 530.

Figure 15:
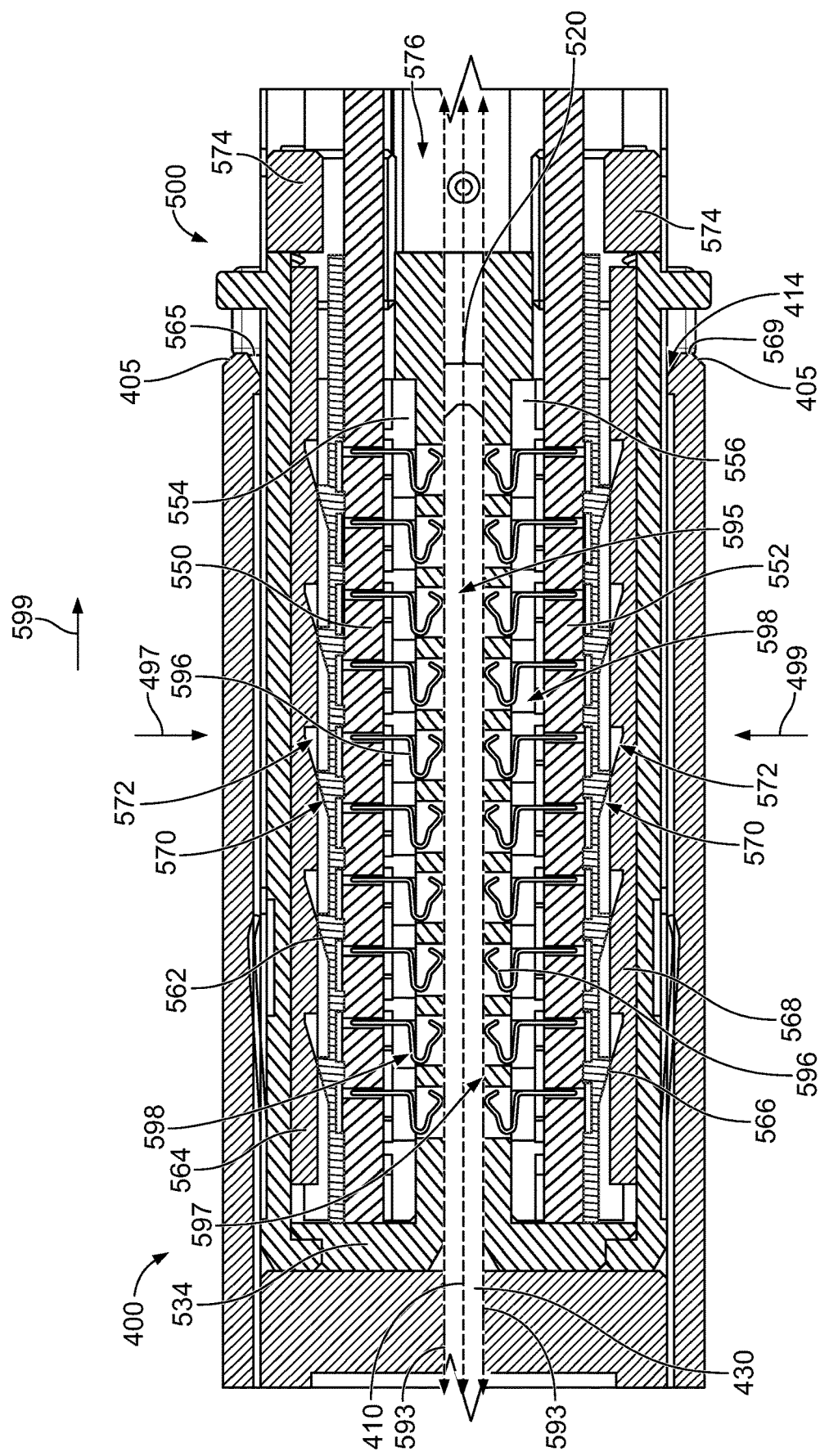
FIG. 15 is a cross-section of the plug connector of FIG. 10 and the receptacle connector of FIG. 12 during a mating operation.

FIG. 15 is a cross-section of the receptacle connector 500 and the plug connector after the plug substrate 430 is inserted into the enclosed slot 520. The backstop portions 574 are positioned within the connector passage 576. The backstop portions 574 may be secured to the connector shield 512. Optionally, projections of the backstop portion 574 extend through openings in the first and second housing shells 514, 516. The projections may provide a positive stop that prevents the backstop portion 574 from moving along the centerline 410 in either direction.

The first cam plate 562 is sandwiched between the first actuator 564 and the first printed circuit 550, which is disposed within the first tray 554. The second cam plate 566 is sandwiched between the second actuator 568 and the second printed circuit 552, which is disposed within the second tray 556. As shown, the ramps 570 of the cam plates are disposed within the corresponding recesses 572 of the actuators. Electrical contacts 596, which may be similar or identical to the electrical contacts 344 (FIG. 8B), are secured to the first and second printed circuits 550, 552 and extend through respective contact openings 598 of the first and second trays 554, 556.

During a mating operation, the plug connector 400 and the receptacle connector 500 are moved relative toward one another such that the plug substrate 430 is inserted into the enclosed slot 520. A leading portion of the receptacle connector 500 is received within the mating cavity 414. As the plug connector 400 moves in the mating direction 599, the interior wall surface 418 slides along an exterior surface 508 of the receptacle connector 500. The front edge 405 of the plug connector 400 engages the engagement surfaces 565, 569. A force moving the plug connector 400 and/or the receptacle connector 500 relative to one another drives the mating operation such that the first and second actuators 564, 568 move in the mating direction 599. As the first and second actuators 564, 568 move in the mating direction 599, the first and second actuators 564, 568 engage the ramps 570 of the first and second cam plates 562, 566, respectively, thereby deflecting or otherwise causing the first and second printed circuits 550, 552 to move toward the enclosed slot 520.

The electrical contacts 596 are secured to the printed circuits 550, 552. As the printed circuits 550, 552 are moved in opposite radial directions 497, 499, respectively, the electrical contacts 596 move through the contact openings 598 and into the enclosed slot 520 where the electrical contacts 596 engage the plug substrate 430. Accordingly, the electrical contacts 596 are movable, as a group, in a corresponding radial direction that is perpendicular to the centerline 410 or to a center plane that intersects the centerline 410 and toward the enclosed slot 520. The electrical contacts 596 are movable, as a group, after the plug substrate 430 has been inserted into the enclosed slot 520. In the illustrated embodiment, the plug substrate 430 may continue to move as the electrical contacts 596 are moved toward the plug substrate 430. The electrical contacts 596 may engage corresponding electrical contacts of the plug substrate 430.

When the plug and receptacle connectors 400, 500 are decoupled, the plug connector 400 moves in a direction that is opposite the mating direction 599. While the plug and receptacle connectors 400, 500 are mated, the biasing members 590 (FIG. 14D) are in compressed conditions. As the front edge 405 of the plug connector 400 moves away, the biasing members 590 move the corresponding actuators in the direction that is opposite the mating direction 599. As the first and second actuators 564, 568 move in the opposite direction, the first and second actuators 564, 568 receive the ramps 570 of the first and second cam plates 562, 566 within respective recesses 572. The ramps 570 and recesses 572 may be shaped to reduce resistance and allow the ramps 570 to move freely into the recesses 572. The biasing members 575 may also facilitate returning the mating mechanism 560 to an unmated state. More specifically, the biasing members 575 may urge the corresponding trays away from the enclosed slot 520 (or carrier 534), thereby pushing the corresponding printed circuit and, consequently, the corresponding cam plate. The electrical contacts 596 may move away from the enclosed slot 520 into respective contact openings of the carrier 534 or the corresponding tray.

In other embodiments, the plug substrate 430 may trigger movement of the first and second printed circuits 550, 552 toward the plug substrate 430. For example, the plug substrate 430 may engage one or more engagement surfaces within the receptacle connector 500, such as within the enclosed slot 520. More specifically, the plug substrate 430 may engage the backstop portion 574 or another portion that is coupled to the actuators causing the first and second actuators 564, 568 to move in a mating direction 599 that is along the centerline 410. As the first and second actuators 564, 568 move in the mating direction 599, the first and second actuators 564, 568 engage the ramps 570 of the first and second cam plates 562, 566, respectively, thereby deflecting or otherwise causing the first and second printed circuits 550, 552 to move toward the enclosed slot 520 as described above.

Accordingly, the matching mechanism of the illustrated embodiment includes an actuator and a cam plate that are operably engaged with each other. A driving force for moving the printed circuit in the radial direction is provided when the plug connector engages the actuator. The actuator is pushed in the mating direction and is operably engaged to the cam plate such that the cam plate is driven in the radial direction. Although the preceding describes one mating mechanism that may be used to move the printed circuit in a radial direction toward the plug substrate, it should be understood that other mechanisms may be used.

Similar to the plug connector 200 (FIG. 3) and the receptacle connector 300 (FIG. 6), the receptacle connector 500 includes system arrays 595, 597 of the electrical contacts 596 and the plug connector 400 includes the mating arrays 416 on opposite sides of the plug substrate 430. The system arrays 595, 597 engage the respective mating arrays 416 on opposite sides of the plug substrate 430. Each of the system arrays 595, 597 engages one of the mating arrays 416 along a respective mating zone 593. Each of the mating zones 593 is within the enclosed slot 520. The mating zones 593 extend essentially parallel to the centerline 410.

Figure 16:
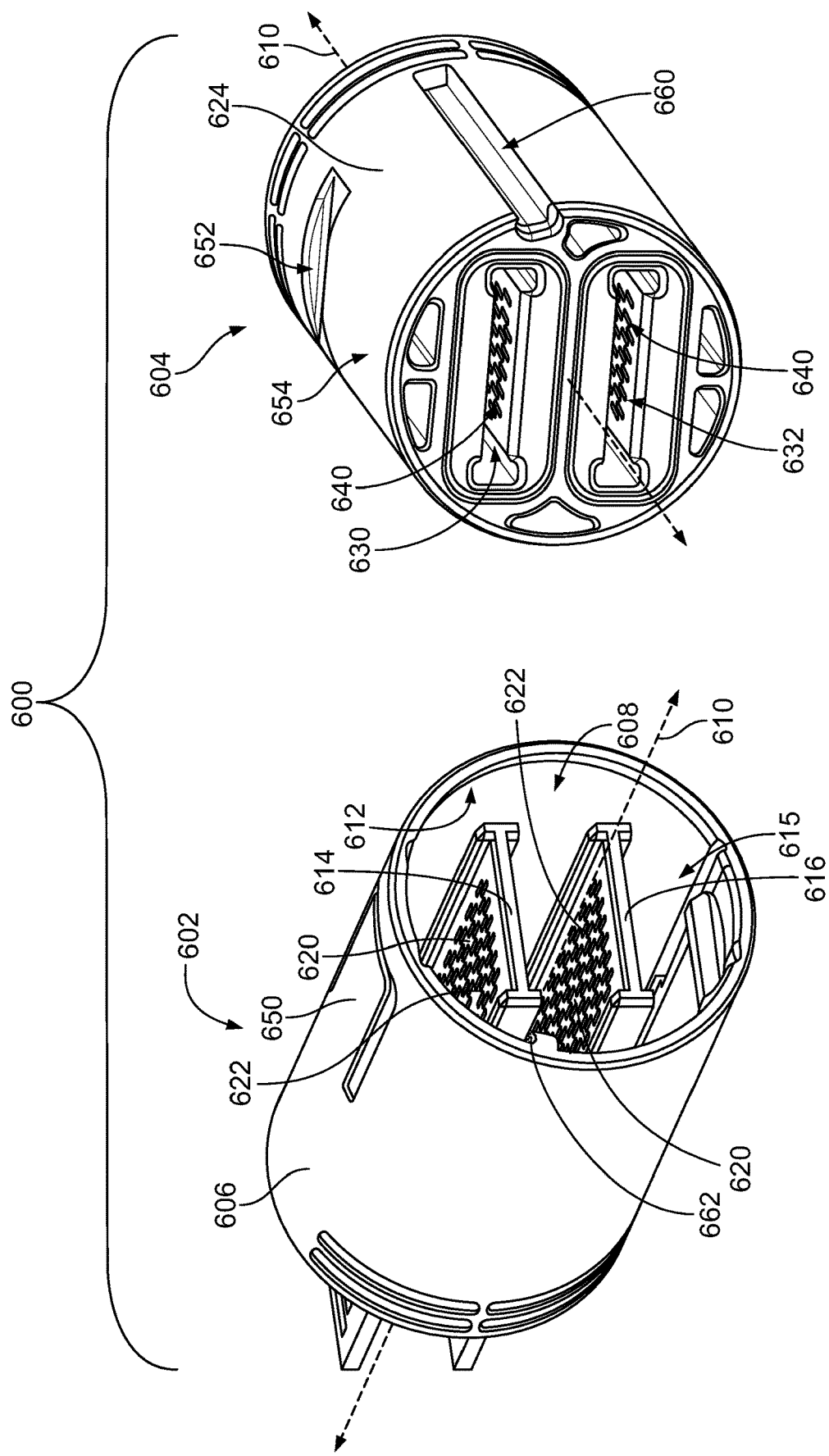
FIG. 16 illustrates a catheter connector assembly that includes a plug connector having two plug substrates and a receptacle connector having two enclosed slots in accordance with an embodiment.

FIG. 16 illustrates a catheter connector assembly 600 that includes a plug connector 602 and a receptacle connector 604. The plug connector 602 includes a plug housing 606 having a mating cavity 608 that is configured to receive the receptacle connector 604. The mating cavity 608 is defined by an interior wall surface 612 that surrounds a centerline 610 of the catheter assembly (not shown). As shown in FIG. 16, the centerline 610 extends through a center of each of the plug and receptacle connectors 602, 604. When the plug and receptacle connectors 602, 604 are mated, the centerlines 610 will coincide with each other and form a single centerline 610.

The plug connector 602 also includes first and second plug substrates 614, 616 that each extend along the centerline 610 within the mating cavity 608 such that a connector-receiving space 615 exists between the first and second plug substrates 614, 616 and the interior wall surface 612. Each of the first and second plug substrates 614, 616 includes at least one contact array 620 of electrical contacts 622. The contact arrays 620 are oriented parallel to the centerline 610.

The receptacle connector 604 includes a receptacle housing 624. The receptacle housing 624 defines first and second enclosed slots 630, 632 that are configured to receive the first and second plug substrates 614, 616, respectively. The enclosed slots 630, 632 open in an axial direction that is parallel to the centerline 610. At least one contact array 640 is exposed within each of the first and second enclosed slots 630, 632. The contact arrays 640 are configured to engage the contact arrays 620 along the plug substrates 614, 616, respectively, within the enclosed slots 630, 632. The contact arrays 620, 640 may engage one another along mating zones as described with respect to FIG. 9B.

Also shown in FIG. 16, the plug housing 606 includes a resilient latch 650, and the receptacle housing 624 includes a latch-receiving space 652. The resilient latch 650 includes an inner contoured head or ramp (not shown). During a mating operation, the contoured head of the resilient latch 650 engages an exterior surface 654 of the receptacle housing 624 such that the resilient latch 650 is partially deflected by the receptacle housing 624 in a radial direction away from the centerline 610. When the contoured head clears the latch-receiving space 652, the resilient latch 650 flexes into the latch-receiving space 652. The contoured head reduces the likelihood that the plug connector 602 and the receptacle connector 604 will inadvertently decouple.

The exterior surface 654 is shaped to form a keying groove or channel 660, and the interior wall surface 612 is shaped to form a ridge 662. The ridge 662 and the keying groove 660 are sized and shaped relative to one another such that the keying groove 660 receives the ridge 662 when the plug connector 602 and the receptacle connector 604 are aligned and properly oriented.

Figure 17:
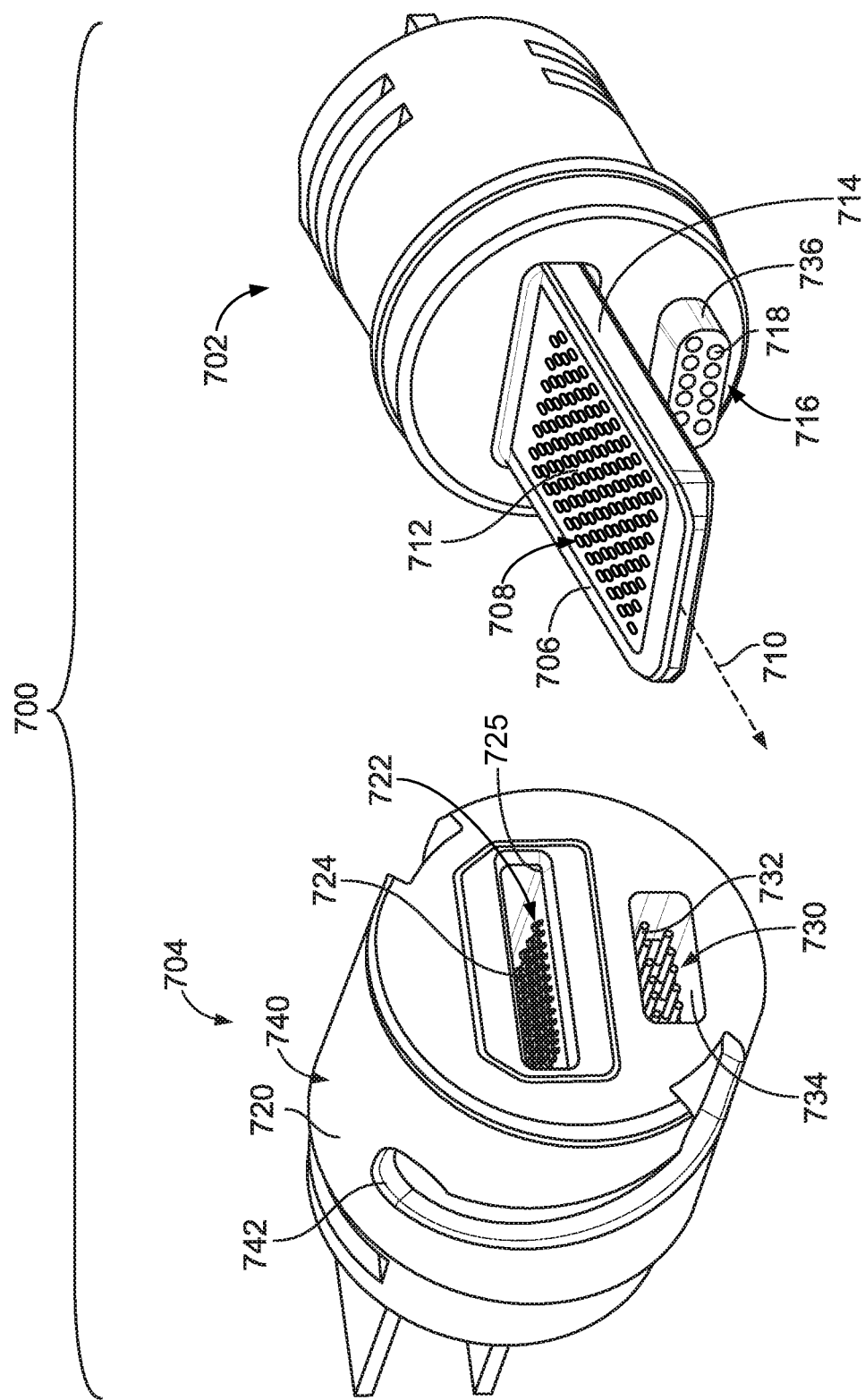
FIG. 17 illustrates a catheter connector assembly that includes a plug connector having a molded plug substrate and a receptacle connector in accordance with an embodiment.

FIG. 17 illustrates a catheter connector assembly 700 that includes a plug connector 702 and a receptacle connector 704. The plug connector 702 includes an elongated plug substrate 706 and a contact array 708 of electrical contacts 712 supported by the plug substrate 706. The plug substrate 706 projects in an axial direction along a centerline 710 of the catheter assembly (not shown). In FIG. 17, the plug substrate 706 is not positioned within a mating cavity and is exposed to an exterior of the plug connector 702. The plug substrate 706 includes a molded support frame 714. The support frame 714 may be configured to enhance a structural integrity of the plug substrate 706 to decrease the likelihood that the plug substrate 706 may be damaged. Also shown, the plug connector 702 includes a secondary array 716 of electrical contacts 718. The secondary array 716 may constitute, for example, a female D-subminiature connector and the electrical contacts 718 may be socket contacts.

The receptacle connector 704 includes a receptacle housing 720 and a contact array 722 of electrical contacts 724. The receptacle housing 720 has an enclosed slot 725 that is sized and shaped to receive the plug substrate 706 during a mating operation in which the plug substrate 706 is inserted into the enclosed slot 725 in the axial direction. The contact array 708 and the contact array 722 engage each other along a mating zone (not shown) within the enclosed slot 725. Each of the contact array 708 and the contact array 722 is planar and extends parallel to the centerline 710. Also shown, the receptacle connector 704 includes a secondary array 730 of electrical contacts 732. The secondary array 730 may constitute, for example, a male D-subminiature connector and the electrical contacts 732 may be pin contacts that are received by the electrical contacts 718 during the mating operation. The secondary array 730 may be surrounded by a shield 734 and may engage a shield 736 of the secondary array 716.

The contact arrays 708, 722 communicate data signals of a one type. The secondary arrays 716, 730 may communicate at least one of electrical power or data signals of a second type. For example, the contact arrays 708, 722 may communicate image data from an ultrasound probe. The secondary arrays 716, 730 may communicate data from an image sensor, data for a designated parameter (e.g., temperature, pressure), or data that may be used to determine an orientation of the modular device. For example, the modular device may include magnetic coils for determining an orientation or estimating motion of the modular device.

Also shown in FIG. 17, an exterior surface 740 of the receptacle housing 720 may define a locking groove 742. The locking groove 742 may be configured to receive a projection from a coupling nut (not shown) in a bayonet style coupling action.

Figure 18:
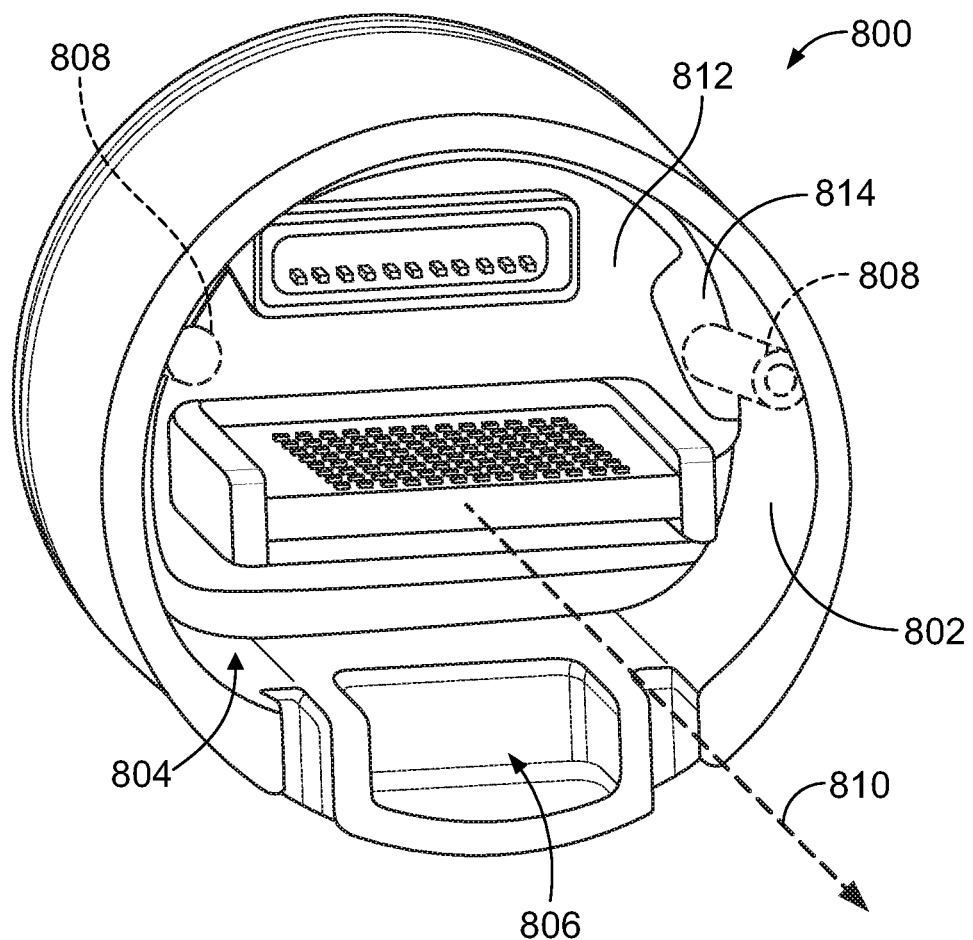
FIG. 18 is a front perspective view of a plug connector formed in accordance with an embodiment having an interior gasket for impeding contamination.

FIG. 18 is a front perspective view of a plug connector 800 formed in accordance with an embodiment. The plug connector 800 may be similar to the plug connector 200

(FIG. 3). For example, the plug connector 800 has an interior wall surface 802. The interior wall surface 802 defines a mating cavity 804 that is sized and shaped to receive at least a portion of another electrical connector. The interior wall surface 802 surrounds a centerline 810 and faces radially-inward toward the centerline 810. In the illustrated embodiment, the interior wall surface 802 is essentially smooth for a majority of the interior wall surface 802 having the same radius of curvature. The interior wall surface 802, however, is shaped to form a latch sub-cavity 806 and keying ridges 808.

Optionally, embodiments may include an interior gasket 812. More specifically, the plug connector 800 includes an interior housing wall 814 that faces in the axial direction. The interior gasket 812 may be positioned along a surface of the interior housing wall 814. In such embodiments, the interior gasket 812 may engage a front end of a receptacle connector (not shown) and establish a seal that protects the mating zones from contaminants or moisture.

Figure 19:
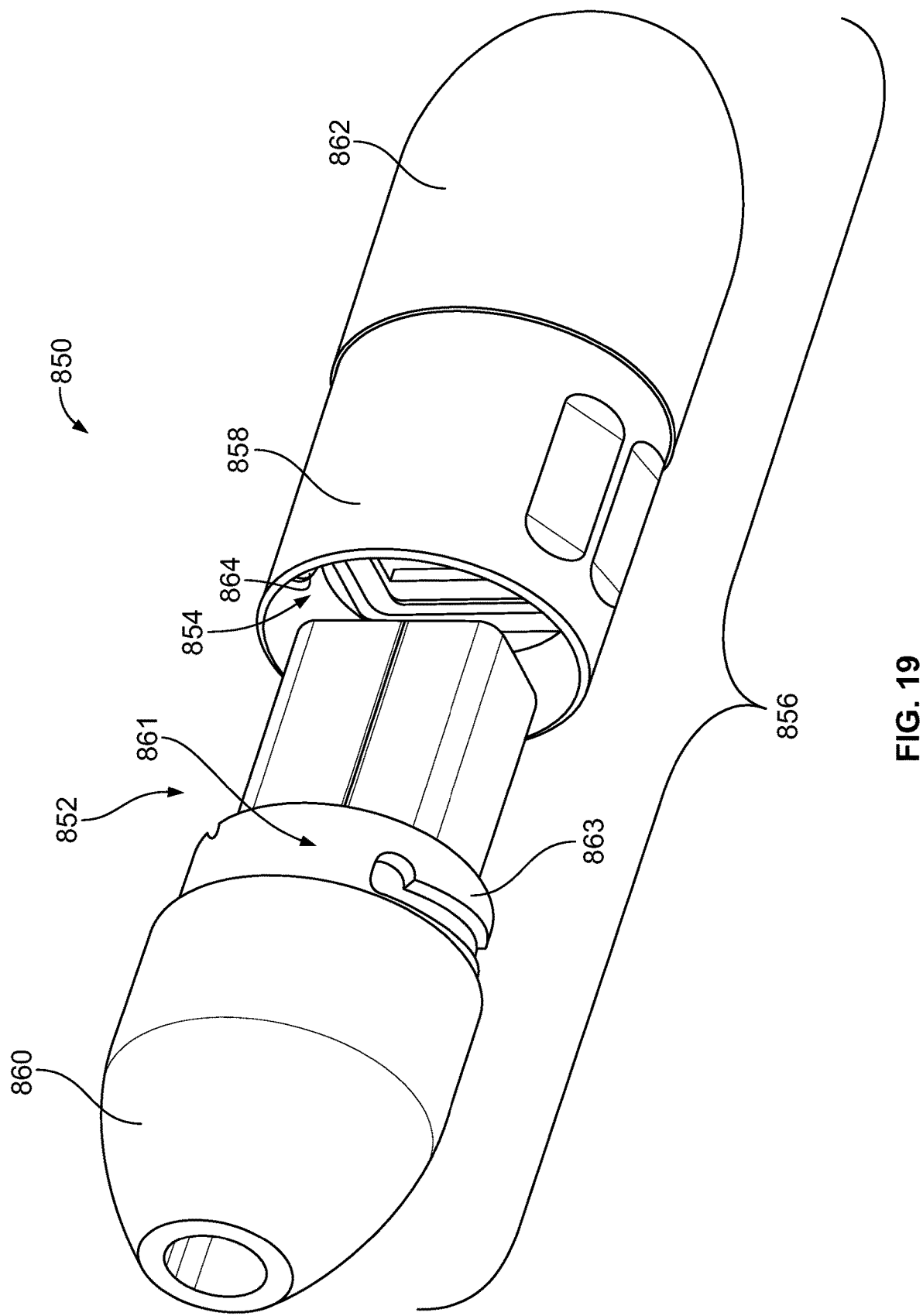
FIG. 19 is a perspective view of a catheter connector assembly formed in accordance an embodiment having a rotatable coupling nut.

FIG. 19 is a perspective view of a catheter connector assembly 850 that includes a plug connector 852 and a receptacle connector 854. The catheter connector assembly 850 also includes a coupling shell assembly 856 that includes a rotatable coupling nut 858 and first and second strain-relief boots 860, 862. The coupling nut 858 is positioned between the first and second strain-relief boots 860, 862 and surrounds the receptacle connector 854. In other embodiments, the coupling nut 858 may surround the plug connector 852.

The coupling shell assembly 856 may include a bayonet-style coupling mechanism. As shown in FIG. 19, an exterior surface 861 of the plug connector 852 defines a locking groove 863. The locking groove 863 is configured to receive an inner projection 864 from the coupling nut 858. As the coupling nut 858 is rotated with the inner projection 864 in the locking groove 863, the plug and receptacle connectors 852, 854 are forced toward one another and fully mated.

Figure 20:
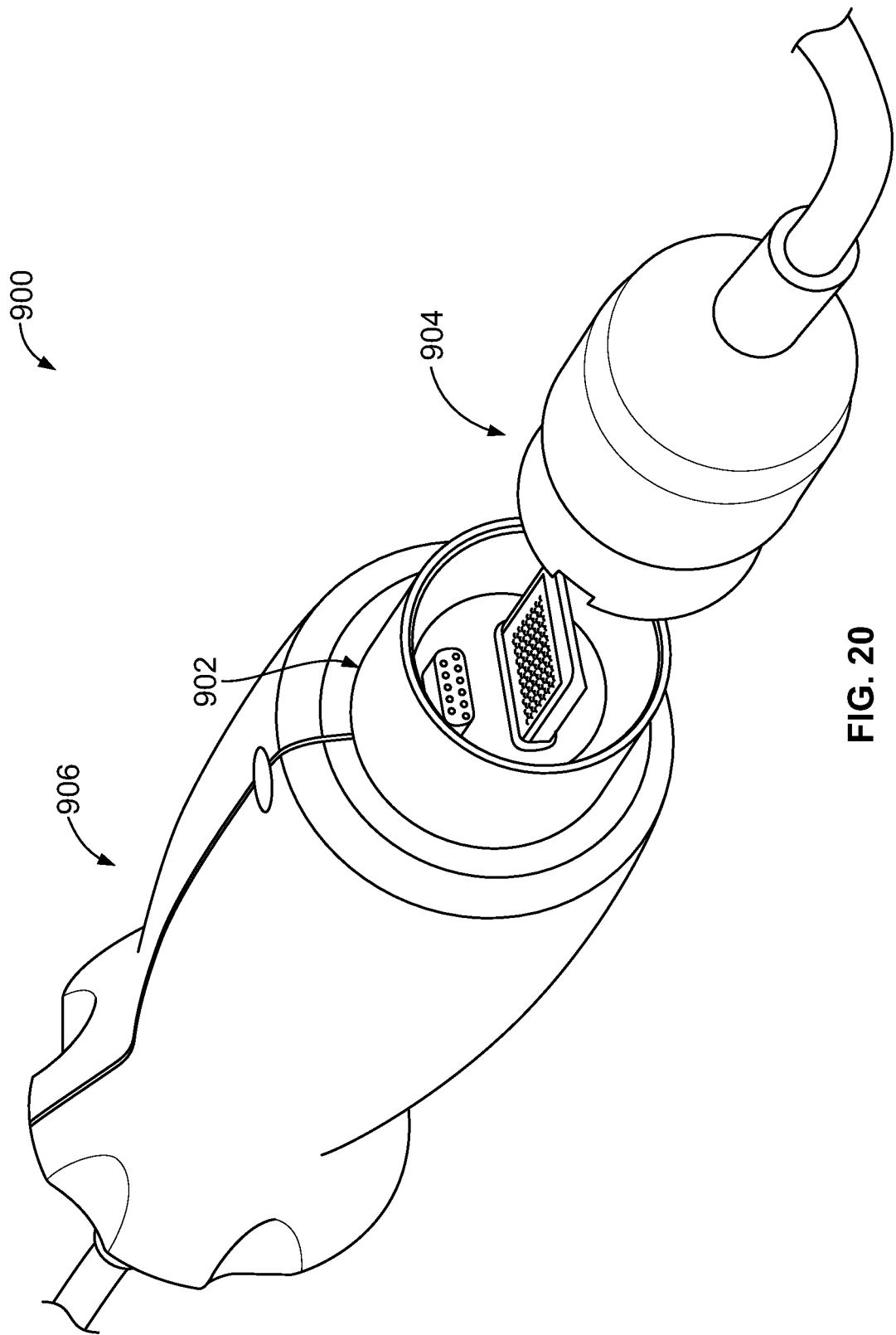
FIG. 20 is a perspective view of a catheter connector assembly formed in accordance an embodiment having an operator handle with an integrated electrical connector.

FIG. 20 is a perspective view of a catheter connector assembly 900 that includes a plug connector 902 and a receptacle connector 904. The plug connector 902 and the receptacle connector 904 may be similar to the plug connectors and receptacle connectors described herein. Optionally, the plug connector 902 may be an integrated component of an operator handle 906. The operator handle 906 may be gripped by an operator and manipulated to control movement and/or functioning of the modular device. Although FIG. 20 illustrates the plug connector 902 being integrated with the operator handle 906, other embodiments may include the receptacle connector 904 integrated with the operator handle 906.

Although embodiments described above include different features, it should be understood that one or more embodiments may include a combination of features. For example, the mating mechanism 560 may be incorporated into the catheter connector assembly 380 (FIG. 9A) or into the catheter connector assemblies 850, 900. As another example, the mating mechanism 560 may be incorporated into a catheter connector assembly that includes an interior gasket, such as the interior gasket 812.

In other embodiments, a catheter connector assembly may include multiple mating zones, but at least some of the mating zones may not be parallel to other mating zones. For example, the plug connector may include three plug substrates that are positioned about the centerline at different radial locations. Each has a side that faces the centerline, but the plug substrates may be angled with respect to one another. For instance, each of the plug substrates may be associated with a perpendicular line extending from the plug substrate to the centerline. The three perpendicular lines may have different angles with respect to the centerline. For example, a first perpendicular line may be at 120 degrees, a second perpendicular line may be at 240 degrees, and a third perpendicular line may be at 360 degrees (or 0 degrees).

Figure 21:
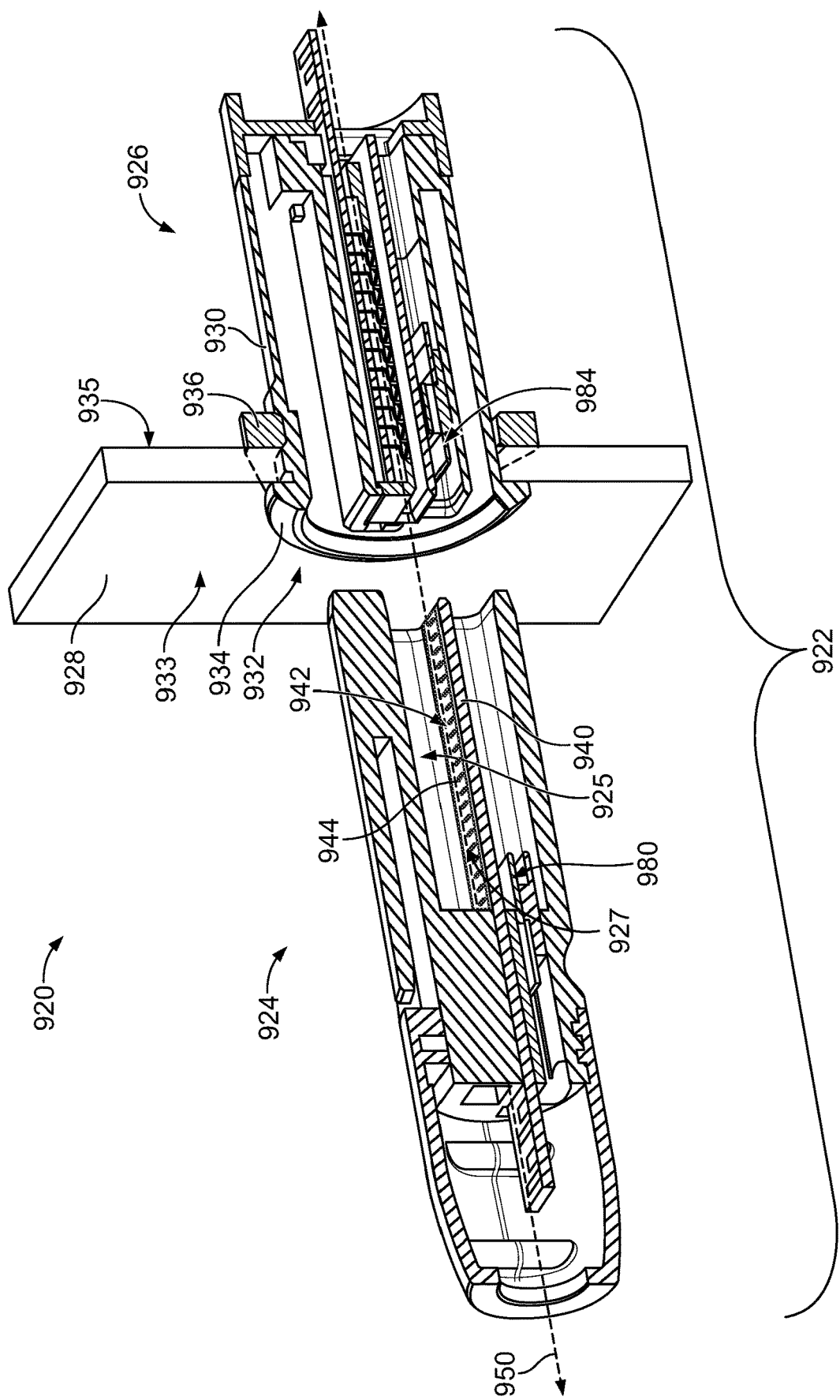
FIG. 21 is a sectional view of a portion of a system having a connector assembly formed in accordance with an embodiment.

FIG. 21 is a sectional view of a portion of a system 920. The system 920 may be similar to the system 100 (FIG. 1). For example, the system 920 includes a catheter connector assembly 922 having a plug connector 924 and a receptacle connector 926. The catheter connector assembly 922 may form part of a catheter assembly, such as the catheter assembly 102 (FIG. 1). Also shown, the system 920 includes a panel 928. The receptacle connector 926 is mounted to the panel 928 and positioned to mate with the plug connector 924. The panel 928 may form part of a control system, such as the control system 104 (FIG. 1). For example, the panel 928 may constitute a side wall of a housing of the control system.

In the illustrated embodiment of FIG. 21, the receptacle connector 926 is mounted to the panel 928. The plug connector 924 may be coupled to an end (e.g., a proximal end) of a cable assembly. In other embodiments, however, a plug connector may be mounted to the panel and a receptacle connector may be coupled to an end of a cable assembly.

The plug connector 924 may be positioned at an end of a cable assembly, such as the cable assembly 108 (FIG. 1) and/or at an end of a cable segment, such as the cable segment 122 (FIG. 1). The plug connector 924 and the receptacle connector 926 interconnect the cable segment and the control system, thereby coupling a modular device (e.g., ultrasound probe) to the control system. In such embodiments, the system 920 may include two or more cable segments or, alternatively, only one cable segment.

As shown in FIG. 21, the receptacle connector 926 includes a receptacle housing 930. The receptacle housing 930 has a mounting end 932. The mounting end 932 includes a rim or flange 934 that is configured to engage a first side 933 of the panel 928. In some embodiments, the system 920 includes hardware 936 (e.g., nut) that engages an opposite second side 935 of the panel 928 to secure the receptacle connector 926 to the panel 928.

As shown in FIG. 21, the plug connector 924 also includes an interior wall surface 925. The interior wall surface 925 defines a mating cavity 927 that is sized and shaped to receive at least a portion of the receptacle connector 926 (FIG. 6). The plug connector 924 includes an elongated plug substrate 940 and a mating array 942 of electrical contacts 944 supported by the plug substrate 940. The plug substrate 940 projects in an axial direction along a centerline 950. The electrical contacts 944 may be similar or identical to other electrical contacts described herein, such as the electrical contacts 228 (FIG. 3).

Also shown in FIG. 21, the plug connector 924 includes a secondary array 980 of electrical contacts, and the receptacle connector 926 includes a secondary array 984 of electrical contacts. The secondary arrays 980, 984 are configured to engage each other during the mating operation. In some embodiments, the mating array 942 and system array 962 may communicate data signals of a first type, and the secondary arrays 980, 984 may communicate at least one of electrical power or data signals of a second type.

Figure 22:
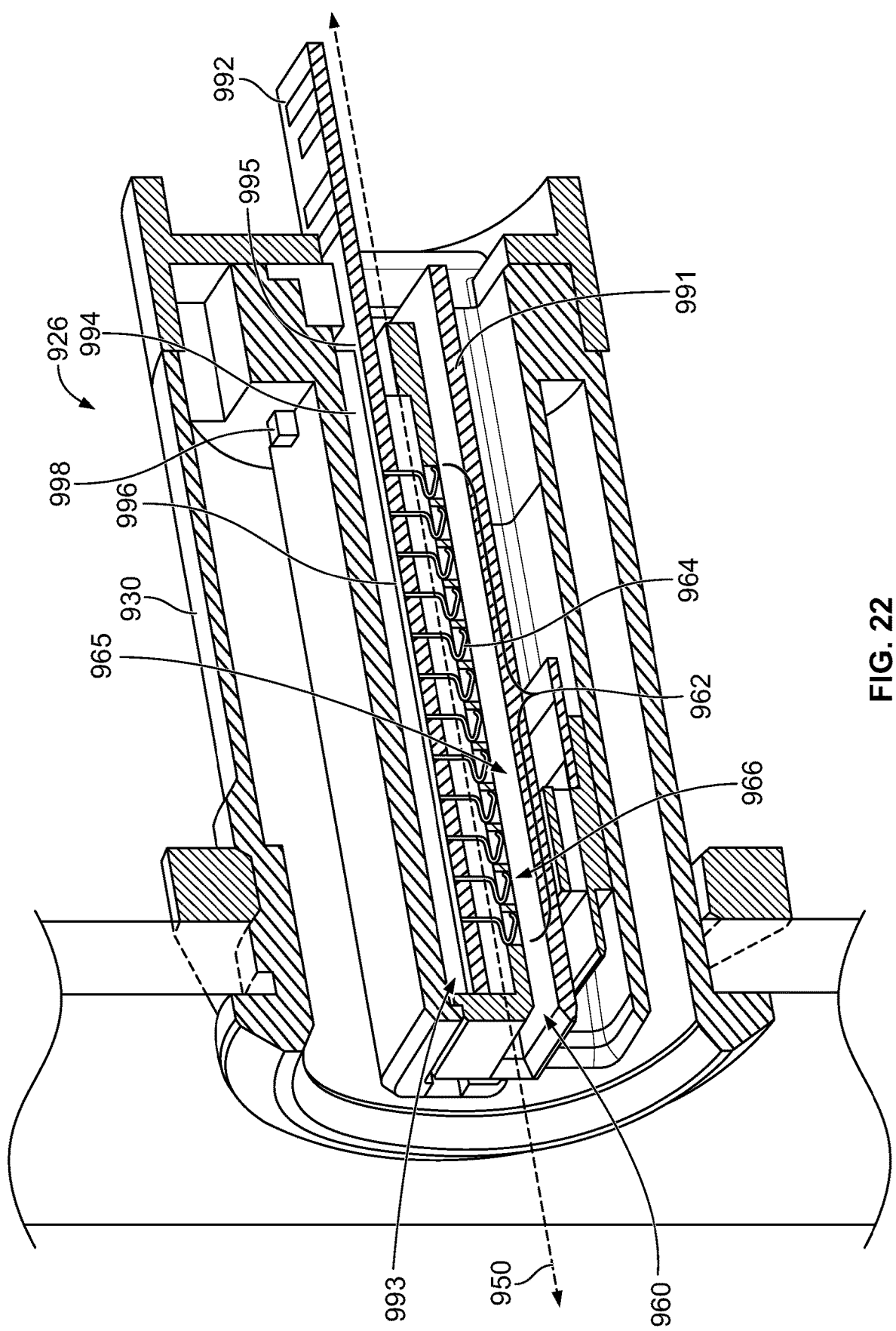
FIG. 22 is an enlarged sectional view of a receptacle connector of the connector assembly of FIG. 21.

FIG. 22 is an enlarged sectional view of the receptacle connector 926. The receptacle connector 926 may have features that are similar or identical to the features described herein with respect to the receptacle connectors 126, 300, 500, 604, 704, 854, 904. For example, the receptacle housing 930 has an enclosed slot 960 that is sized and shaped to receive the plug substrate 940 (FIG. 21) during a mating operation in which the plug substrate 940 is inserted into the enclosed slot 960 in an axial direction. The receptacle connector 926 includes a system array 962 of electrical contacts 964 positioned along a mating zone 966 within the enclosed slot 960. The enclosed slot 960 is partially defined by an interior wall 965. The interior wall 965 opposes the system array 962 and is devoid of electrical contacts.

The system array 962 and the mating array 942 are configured to engage each other along the mating zone 966 within the enclosed slot 960. In some embodiments, each of the system array 962 and the mating array 942 may include at least 40 electrical contacts that are coplanar with respect to the other electrical contacts of the respective array. The electrical contacts 964 may be similar or identical to other electrical contacts described herein, such as the electrical contacts 344 (FIG. 8B). The electrical contacts 964 and the electrical contacts 944 (FIG. 21) may engage one another in a similar manner as described with respect to FIGS. 9A and 9B.

In some embodiments, the electrical contacts 964 of the system array 962 are movable, as a group, in a radial direction that is perpendicular to the centerline 950. For example, the receptacle connector 926 may include a circuit sub-assembly 990 that is similar to a portion of the circuit sub-assembly 535 (FIG. 14A). For example, the circuit sub-assembly 990 may include a tray 991 that includes the interior wall 965, a printed circuit 992 having the system array 962, and a mating mechanism 993. The mating mechanism 993 is configured to move the printed circuit 992 toward the enclosed slot 960 or toward the interior wall 965. In particular embodiments, the mating mechanism 993 includes a cam plate 994 and an actuator 995. The cam plate 994 is positioned side-by-side and forms a slidable interface with the actuator 995. The cam plate 994 includes ramps 996, and the actuator 995 includes recesses 997 that receive the ramps 996. The actuator 995 also includes an engagement surface 998.

During a mating operation, the plug connector 924 (FIG. 21) and the receptacle connector 926 are moved relative toward one another such that the plug substrate 940 is inserted into the enclosed slot 960. The plug connector 924 engages the engagement surface 998, thereby driving the actuator 994 in the mating direction. As the actuator 995 moves in the mating direction, the actuator 995 engages the ramps 996, thereby deflecting or otherwise causing the printed circuit 992 to move toward the enclosed slot 960. The electrical contacts 964 move with the printed circuit 992 and engage respective electrical contacts 944 (FIG. 21).

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The patentable scope should, therefore, be determined with reference to the appended claims, along with the full scope of equivalents to which such claims are entitled.

As used in the description, the phrase "in an exemplary embodiment" and the like means that the described embodiment is just one example. The phrase is not intended to limit the inventive subject matter to that embodiment. Other embodiments of the inventive subject matter may not include the recited feature or structure. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An electrical system comprising:
a control system and a modular device communicatively coupled through a cable assembly and a connector assembly, the modular device configured to be inserted into a body and configured to at least one of detect external signals or emit energy, the connector assembly having a plug connector and a receptacle connector, wherein a centerline extends through the cable assembly;
the plug connector comprising an elongated plug substrate and a mating array of electrical contacts supported by the plug substrate, the plug substrate projecting in an axial direction along the centerline; and
the receptacle connector comprising a receptacle housing and a system array of electrical contacts, the receptacle housing having an enclosed slot that is sized and shaped to receive the plug substrate during a mating operation in which the plug substrate is inserted into the enclosed slot in the axial direction, the electrical contacts of each of the system array and the mating array being positioned along at least first and second dimensions such that, for each of the system array and the mating array, at least some of the electrical contacts are spaced apart along a length of the respective array and at least some of the electrical contacts are spaced apart along a width of the respective array, the length of the respective array being parallel to the centerline, wherein the system array and the mating array engage each other along a mating zone within the enclosed slot, the mating zone extending essentially parallel to the centerline.

2. The electrical system of claim 1, wherein the electrical contacts of at least one of the system array or the mating array includes mating segments, the mating segments being deflected along the mating zone.

3. The electrical system of claim 2, wherein the enclosed slot is defined by an interior slot surface, the mating segments including spring fingers that clear the interior slot surface and are deflected toward the interior slot surface.

4. The electrical system of claim 1, wherein the plug connector includes a plug housing having a mating cavity that is configured to receive the receptacle connector, the mating cavity being defined by an interior wall surface that surrounds the centerline, the plug housing and the receptacle housing configured to pluggably engage each other such that the interior wall surface surrounds the receptacle housing.

5. The electrical system of claim 1, wherein the mating array includes at least 40 electrical contacts that are coplanar with respect to one another, the connector assembly having an outer diameter at the plug connector that is at most 45 millimeters (mm).

6. The electrical system of claim 1, wherein the electrical contacts of the system array are movable, as a group, in a radial direction that is perpendicular to the centerline.

7. The electrical system of claim 1, wherein each of the plug connector and the receptacle connector include a secondary array of electrical contacts, the secondary arrays engaging each other during the mating operation, wherein the mating array and system array communicate data signals of a first type, the secondary arrays communicating at least one of electrical power or data signals of a second type, the plug connector and the receptacle connector comprising internal shields that surround the secondary arrays when mated.

8. A kit comprising the electrical system of claim 1, wherein the cable assembly includes first and second cable segments that are interconnected by the plug connector and the receptacle connector, the first cable segment being a single-use disposable segment, the kit including a plurality of the first cable segments that are each configured to operably engage the second cable segment.

9. The electrical system of claim 1, wherein the electrical contacts of the mating array coincide with a mating plane and the electrical contacts of the system array coincide with a system plane, the mating and system planes extending parallel to the centerline.

10. The electrical system of claim 1, wherein the plug substrate includes first and second guide walls and the enclosed slot has first and second guide channels that are sized and shaped to receive the first and second guide walls, respectively, the first and second guide walls having an increased thickness relative to a middle portion of the plug substrate that includes the mating array and that extends between the first and second guide walls.

11. The electrical system of claim 1, wherein the plug connector includes an interior base surface that faces in the axial direction, the plug substrate projecting from the interior base surface in the axial direction.

12. The electrical system of claim 11, wherein the plug connector further comprises a secondary array of the electrical contacts, the secondary array of the electrical contacts projecting from the interior base surface in the axial direction such that a gap exists between the plug substrate and the secondary array.

13. The electrical system of claim 12, wherein the plug connector further comprises an internal shield that projects from the interior base surface such that the internal shield extends into a mating cavity, the internal shield surrounding the secondary array of the electrical contacts within the mating cavity.

14. The electrical system of claim 11, wherein the plug connector further comprises an interior gasket positioned along the interior base surface, the interior gasket being positioned to engage a front end of the receptacle connector.

15. An electrical cable segment of a catheter assembly, the electrical cable segment comprising:
   an elongated cable extending between an operating end and a mating end, the elongated cable having conductive pathways extending between the operating end and the mating end, wherein a centerline extends through a center of the elongated cable;
   a plug connector coupled to the elongated cable at the mating end, the plug connector including a plug housing having a mating cavity that is configured to receive another connector, the mating cavity being defined by an interior wall surface that surrounds the centerline, the plug connector also including a plug substrate extending along the centerline within the mating cavity such that a connector-receiving space circumscribes the plug substrate, the plug substrate supporting electrical contacts that form a mating array along a surface of the plug substrate, the electrical contacts of the mating array being positioned along at least first and second dimensions such that at least some of the electrical contacts are spaced apart along a length of the mating array and at least some of the electrical contacts are spaced apart along a width of the mating array, the length of the mating array being parallel to the centerline.

16. The electrical cable segment of claim 15, wherein the mating array includes at least 40 electrical contacts that are coplanar with respect to one another, the catheter assembly having an outer diameter at the plug connector that is at most 45 millimeters (mm).

17. The electrical cable segment of claim 15, wherein the cable segment is a single-use disposable segment.

18. The electrical cable segment of claim 15, wherein the plug substrate includes a support frame and a printed circuit that is supported by the support frame, the support frame including first and second guide walls, the printed circuit including the mating array and being positioned between the first and second guide walls of the support frame.

19. The electrical cable segment of claim 15, wherein the plug connector has a loading end that couples to the mating end of the elongated cable, the plug connector including a terminal array proximate to the loading end, the terminal array being positioned along at least the first and second dimensions such that at least some of the electrical contacts are spaced apart along a length of the terminal array and at least some of the electrical contacts are spaced apart along a width of the terminal array, the length of the terminal array being parallel to the centerline, the terminal contacts of the terminal array being electrically connected to the electrical contacts of the mating array.

20. An electrical cable segment of a catheter assembly, the electrical cable segment comprising:
   an elongated cable extending between an operating end and a mating end, the elongated cable having conductive pathways extending between the operating end and the mating end, wherein a centerline extends through a center of the elongated cable;
   a receptacle connector comprising a receptacle housing and electrical contacts that form a system array of the electrical contacts, wherein the receptacle housing has an interior slot surface that defines an enclosed slot that is sized and shaped to receive a plug substrate from another connector, the enclosed slot opening in an axial direction that is parallel to the centerline, wherein the system array is formed along the interior slot surface and is configured to engage a mating array along the plug substrate within the enclosed slot, the system array being positioned along at least first and second dimensions such that at least some of the electrical contacts are spaced apart along a length of the system array and at least some of the electrical contacts are spaced apart along a width of the system array, the length of the system array being parallel to the centerline.

21. The electrical cable segment of claim 20, wherein the electrical contacts of the system array include mating segments, the enclosed slot being defined by an interior slot surface, the mating segments configured to clear the interior slot surface and be deflected toward the interior slot surface.

22. The electrical cable segment of claim 20, wherein the electrical contacts of the system array are movable, as a group, in a radial direction that is perpendicular to the centerline.

23. The electrical cable segment of claim 20, wherein the mating array includes at least 40 electrical contacts that are coplanar with respect to one another, the catheter assembly having an outer diameter at the plug connector that is at most 45 millimeters (mm).

* * * * *